US009725750B2

(12) United States Patent
Kawakami et al.

(10) Patent No.: US 9,725,750 B2
(45) Date of Patent: *Aug. 8, 2017

(54) PROTEIN PRODUCTION METHOD

(71) Applicants:KYOWA HAKKO KIRIN CO., LTD, Tokyo (JP); Inter-University Research-Institute Corporation Research Organization of Information and Systems, Tachikawa-shi, Tokyo (JP)

(72) Inventors: Koichi Kawakami, Mishima (JP); Keina Yamaguchi, Takasaki (JP); Risa Ogawa, Takasaki (JP); Masayoshi Tsukahara, Takasaki (JP)

(73) Assignees: KYOWA HAKKO KIRIN CO., LTD, Tokyo (JP); Inter-University Research Institute Corporation Research Organization of Information and Systems, Tokyo (JP)

( * ) Notice: Subject to any disclaimer, the term of this patent is extended or adjusted under 35 U.S.C. 154(b) by 290 days.

This patent is subject to a terminal disclaimer.

(21) Appl. No.: 14/689,782

(22) Filed: Apr. 17, 2015

(65) Prior Publication Data

US 2015/0218610 A1    Aug. 6, 2015

Related U.S. Application Data

(63) Continuation of application No. 12/813,920, filed on Jun. 11, 2010, now Pat. No. 9,034,649.

(60) Provisional application No. 61/186,138, filed on Jun. 11, 2009.

(30) Foreign Application Priority Data

Jun. 11, 2009  (JP) ................................ 2009-140626

(51) Int. Cl.
| | |
|---|---|
| *C12P 21/00* | (2006.01) |
| *C12P 21/02* | (2006.01) |
| *C12N 15/63* | (2006.01) |
| *C12N 15/85* | (2006.01) |
| *C12N 15/89* | (2006.01) |
| *C12Q 1/68* | (2006.01) |
| *C12N 5/07* | (2010.01) |
| *C07K 16/10* | (2006.01) |

(52) U.S. Cl.
CPC .......... *C12P 21/00* (2013.01); *C07K 16/1018* (2013.01); *C12N 15/85* (2013.01); *C12P 21/02* (2013.01); *C12N 2015/8518* (2013.01); *C12N 2800/107* (2013.01); *C12N 2800/90* (2013.01); *C12N 2840/20* (2013.01)

(58) Field of Classification Search
None
See application file for complete search history.

(56) References Cited

U.S. PATENT DOCUMENTS

| | | | |
|---|---|---|---|
| 6,291,243 B1 | 9/2001 | Fogarty et al. | |
| 6,475,798 B2 | 11/2002 | Fogarty et al. | |
| 7,064,194 B2 | 6/2006 | Misawa et al. | |
| 7,195,915 B2 | 3/2007 | Misawa et al. | |
| 7,737,325 B2 | 6/2010 | Kanda et al. | |
| 2002/0028513 A1 | 3/2002 | Fogarty et al. | |
| 2003/0037346 A1 | 2/2003 | Craig et al. | |
| 2004/0029229 A1 | 2/2004 | Reeves et al. | |
| 2004/0242512 A1 | 12/2004 | Misawa et al. | |
| 2005/0177890 A1 | 8/2005 | Kawakami | |
| 2006/0078992 A1 | 4/2006 | Misawa et al. | |
| 2006/0141627 A1 | 6/2006 | Comer | |
| 2010/0129914 A1 | 5/2010 | Koga et al. | |
| 2010/0311116 A1 | 12/2010 | Wurm et al. | |

FOREIGN PATENT DOCUMENTS

| | | |
|---|---|---|
| JP | 2003235575 A | 8/2003 |
| WO | 00/65042 A1 | 11/2000 |
| WO | 0194571 A1 | 12/2001 |
| WO | 02072843 A1 | 9/2002 |
| WO | 2004016792 A1 | 2/2004 |
| WO | 2007/082164 A2 | 7/2007 |
| WO | 2008/072540 A1 | 6/2008 |
| WO | 2008100424 A2 | 8/2008 |

(Continued)

OTHER PUBLICATIONS

Huang et al., "Gene Transfer Efficiency and Genome-Wide Integration Profiling of Sleeping Beauty, Tol2, and PiggyBac Transposons in Human Primary T Cells", The American Society of Gene & Cell Therapy, Oct. 2010, pp. 1803-1813,vol. 18 No. 10, Minneapolis, Minnesota, USA.
Kawakami, K. "Tol2: a versatile gene transfer vector in vertebrates", Genome Biology, 2007, vol. 8 (Suppl 1), pp. S7.1-S7.10.
Urasaki, A. et., al. "Functional Dissection of the Tol2 Transposable Element Identified the Minimal cis-Sequence and a Highly Repetitive Sequence in the Subterminal Region Essential for Transportation", Genetics Society of America, Oct. 2006, vol. 174. pp. 639-649.
Koga, A. et., al. "Germline Transgenesis of Zebrafish Using the Medaka Tol1 Transposon System", Development Dynamics, 2008, vol. 237, pp. 2466-2474.

(Continued)

*Primary Examiner* — Suzanne M Noakes
*Assistant Examiner* — Jae W Lee
(74) *Attorney, Agent, or Firm* — Sughrue Mion, PLLC

(57) ABSTRACT

This invention relates to a method for producing a protein of interest, comprising introducing a protein expression vector which comprises a gene fragment a gene fragment comprising a DNA encoding a protein of interest and a selectable marker gene and transposon sequences at both terminals of the gene fragment, into a suspension mammalian cell; integrating the gene fragment inserted between a pair of the transposon sequences, into a chromosome of the mammalian cell to obtain a mammalian cell capable of expressing the protein of interest; and suspension-culturing the mammalian cell; and a suspension mammalian cell capable of expressing the protein of interest.

18 Claims, 7 Drawing Sheets

(56) References Cited

FOREIGN PATENT DOCUMENTS

| | | |
|---|---|---|
| WO | 2009/046978 A1 | 4/2009 |
| WO | 2009071334 A2 | 6/2009 |

OTHER PUBLICATIONS

Koga, A. et., al. "The Tol1 element of medaka fish is transposed with only terminal regions and can deliver large DNA fragments into the chromosomes", Journal of Human Genetics, 2007, vol. 52, pp. 1026-1030.
Koga, A. et., al. "The Tol1 transposable element of the medaka fish moves in human and mouse cells", Journal of Human Genetics, 2007, vol. 52, pp. 628-635.
Kodama, K. et., al. "The Tol1 element of the medaka fish, a member of the hAT transposable element family, jumps in Caenorhabditis elegans", Heredity, 2008, vol. 101, pp. 222-227.
Koo, T. Y. et., al. "Beneficial effect of 30Kc6 gene expression on production of recombinant interferon-B in serum-free suspension culture of CHO cells", Process Biochemistry, Feb. 2009, vol. 44, pp. 146-153.
Koga, A. et., al. "Transposable element in fish", Sep. 1996, Nature, vol. 383, p. 30.
Ivics, Z. et., al. "Molecular Reconstruction of sleeping Beauty, a Tc1-like Transposon from Fish, and Its Transposition in Human Cells", Cell, 1997, vol. 91, pp. 501-510.
Fraser, M. J. et., al. "Precise excision of TTAA-specific lepidopteran transposons piggyBac (IFP2) and tagalong (TFP3) from the baculovirus genome in cell lines two species of *Lepidoptera*", Insect Molecular Biology, 1998, vol. 5(2), pp. 141-151.
Kawakami, K. et., al. "Transposition of the Tol2 Element, an Ac-Like Element From the Japanese Medaka Fish *Oryzias latipes* in Mouse Embryonic Stem Cells", Genetics Society of America, Feb. 2004, vol. 166, pp. 895-899.
Balciunas. D. et., al. "Harnessing a High Cargo-Capacity Transposon for Genetic Applications in Vertebrates", PLOS Genetics, Nov. 2006, vol. 2, Issue 11, pp. 1715-1724.
Fischer, S. E. J. et., al. "Regulated transposition of a fish transposon in the mouse germ line", PNAS, Jun. 5, 2001, vol. 98, No. 12, pp. 6759-6764.
Dupuy, A. J. et., al. "Mammalian mutagenesis using a highly mobile somatic Sleeping Beauty transposon system", Nature, Jul. 14, 2005, vol. 436. pp. 221-226.
Cadiñanos, J. et., al. "Generation of an inducible and optimized piggyBac transposon system", Nucleic Acids Research, Jun. 18, 2007, vol. 35, No. 12, pp. 1-8.
Schifferli, K. P. et., al. "Transfection of Suspension Cultures of CHO Cells", Focus, vol. 21, No. 1, pp. 16-17.
Wu, S. Chiung-Yuan et., al. "piggyBac is a flexible and highly active transposon as compared to Sleeping Beauty, Tol2, and Most in mammalian cells", PNAS, Oct. 10, 2006, vol. 103, No. 41, pp. 15008-15013.
PCT/ISA/210 issued on Jul. 13, 2010 in corresponding Japanese Patent Application No. PCT/JP2010/059881.
PCT/ISA/237 issued Jul. 13, 2010 in corresponding Japanese Patent Application No. PCT/JP2010/059881.
Miskey, C. et., al. "The Frog Prince: a reconstructed transposon from Rana pipiens with high transpositional activity in vertebrate cells", Nucleic Acids Research, 2003, vol. 31, No. 23, pp. 6873-6881.
Luo, G. et., al. "Chromosomal transposition of a Tc1/mariner-like element in mouse embryonic stem cells", The National Academy of Sciences, Sep. 2008, vol. 95, pp. 10769-10773.
Communication from the European Patent Office issued Dec. 6, 2013 in counterpart European Patent Office 10786229.4.
Office Action, dated May 2, 2013, issued by the State Intellectual Property Office of the People's Republic of China in counterpart Chinese Application No. 201080026008.5.
Office Action, dated Sep. 9, 2013, issued by the United States Patent and Trademark Office, in counterpart U.S. Appl. No. 13/326,873.
Lattenmayer, et al. "Protein-Free Transfection of CHO Host Cells With an IgG-Fusion Protein: Selection and Characterization of Stable High Producers and Comparison to Conventionally Transfected Clones", Biotechnology and Bioengineering, vol. 96, No. 6 Apr. 15, 2007, p. 1118-1126.
Poche, et al. "Resistance against Cycloheximide in Cell Lines from Chinese Hamster and Human Cells is Conferred by the Large Subunit of Cytoplasmic Ribosomes", Molec. gen. Genet. 175, p. 181-185, 1979.
U.S. Patent & Trademark Office, Communication dated Sep. 9, 2013, issued in corresponding U.S. Appl. No. 13/326,873.
U.S. Patent and Trademark Office, Communication dated May 30, 2013, issued in corresponding U.S. Appl. No. 13/326,873.
"Amendment Under 37 C.F.R. § 1.111," Submitted to U.S. Patent and Trademark Office on Jan. 9, 2014 in response to Non-Final Office Action dated Sep. 9, 2013.
"Response to Restriction Requirement," Submitted to the U.S. Patent and Trademark Office on Jun. 28, 2013 in response to Restriction Requirement dated May 30, 2013.
Office Action, dated Mar. 14, 2014, issued by the State Intellectual Property Office of P.R. China in counterpart Chinese Patent Application No. 201080026008.5.
Office Action dated Sep. 26, 2014, issued by the Taiwanese Intellectual Property Office in counterpart Taiwanese Application No. 099119233.
Kwan et al., "The Tol2kit: A Multisite Gateway-Based Construction Kit for Tol2 Transposon Transgenesis Constructs", Developmental Dynamics 2007, p. 3088-3099.

SEQUENCE LISTING

```
<160> NUMBER OF SEQ ID NOS: 17

<210> SEQ ID NO 1
<211> LENGTH: 2788
<212> TYPE: DNA
<213> ORGANISM: Artificial
<220> FEATURE:
<223> OTHER INFORMATION: Synthetic construct of nonautologus Tol2
      transposon

<400> SEQUENCE: 1
cagaggtgta aagtacttga gtaattttac ttgattactg tacttaagta ttatttttgg      60
ggatttttac tttacttgag tacaattaaa aatcaatact tttactttta cttaattaca     120 ttttttttaga aaaaaagta ctttttactc cttacaattt tatttacagt caaaaagtac    180
ttattttttg gagatcactt cattctattt tcccttgcta ttaccaaacc aattgaattg     240
cgctgatgcc cagtttaatt taaatgttat ttattctgcc tatgaaaatc gttttcacat     300
tatatgaaat tggtcagaca tgttcattgg tcctttggaa gtgacgtcat gtcacatcta    360
ttaccacaat gcacagcacc ttgacctgga aattagggaa attataacag tcaatcagtg     420
gaagaaaatg gaggaagtat gtgattcatc agcagctgcg agcagcacag tccaaaatca    480
gccacaggat caagagcacc cgtggccgta tcttcgcgaa ttcttttctt taagtggtgt    540
aaataaagat tcattcaaga tgaaatgtgt cctctgtctc ccgcttaata aagaaatatc    600
ggccttcaaa agttcgccat caaacctaag gaagcatatt gaggtaagta cattaagtat    660
tttgttttac tgatagtttt tttttttttt tttttttttt ttttgggtg tgcatgtttt      720 gacgttgatg gcgcgccttt tatatgtgta gtaggcctat tttcactaat gcatgcgatt     780
gacaatataa ggctcacgta ataaaatgct aaaatgcatt tgtaattggt aacgttaggt    840
ccacgggaaa tttggcgcct attgcagctt tgaataatca ttatcattcc gtgctctcat     900
tgtgtttgaa ttcatgcaaa acacaagaaa accaagcgag aaattttttt ccaaacatgt    960
```

```
tgtattgtca aaacggtaac actttacaat gaggttgatt agttcatgta ttaactaaca    1020
ttaaataacc atgagcaata catttgttac tgtatctgtt aatctttgtt aacgttagtt    1080
aatagaaata cagatgttca ttgtttgttc atgttagttc acagtgcatt aactaatgtt    1140
aacaagatat aaagtattag taaatgttga aattaacatg tatacgtgca gttcattatt    1200
agttcatgtt aactaatgta gttaactaac gaaccttatt gtaaagtgt  taccatcaaa    1260 actaatgtaa tgaaatcaat tcaccctgtc atgtcagcct tacagtcctg tgttttgtc    1320 aatataatca gaaataaaat taatgtttga ttgtcactaa atgctactgt atttctaaaa    1380
tcaacaagta tttaacatta taaagtgtgc aattggctgc aaatgtcagt tttattaaag    1440
ggttagttca cccaaaaatg aaaataatgt cattaatgac tcgccctcat gtcgttccaa    1500
gcccgtaaga cctccgttca tcttcagaac acagtttaag atattttaga tttagtccga    1560
gagctttctg tgcctccatt gagaatgtat gtacggtata ctgtccatgt ccagaaaggt    1620
aataaaaaca tcaaagtagt ccatgtgaca tcagtgggtt agttagaatt ttttgaagca    1680
tcgaatacat tttggtccaa aaataacaaa acctacgact ttattcggca ttgtattctc    1740
ttccgggtct gttgtcaatc cgcgttcacg acttcgcagt gacgctacaa tgctgaataa    1800
agtcgtaggt tttgttattt ttggaccaaa atgtattttc gatgcttcaa ataattctac    1860 ctaaccccact gatgtcacat ggactacttt gatgttttta ttacctttct ggacatggac    1920
agtataccgt acatacattt tcagtggagg gacagaaagc tctcggacta aatctaaaat    1980
atcttaaact gtgttccgaa gatgaacgga ggtgttacgg gcttggaacg acatgagggt    2040
gagtcattaa tgcatctctt tcattttttgg gtgaactaac cctttaatgc tgtaatcaga    2100
gagtgtatgt gtaattgtta catttattgc atacaatata aatatttatt tgttgttttt    2160
acagagaatg cacccaaatt acctcaaaaa ctactctaaa ttgacagcac agaagagaaa    2220
gatcgggaca gatctcatat gctcgagggc ccatctggcc tgtgtttcag acaccaggga    2280
gtctctgctc acgtttcctg ctatttgcag cctctctatc aagactaata cacctcttcc    2340
cgcatcggct gcctgtgaga ggcttttcag cactgcagga ttgcttttca gccccaaaag    2400
agctaggctt gacactaaca attttgagaa tcagcttcta ctgaagttaa atctgaggtt    2460
ttacaacttt gagtagcgtg tactggcatt agattgtctg tcttatagtt tgataattaa    2520
atacaaacag ttctaaagca ggataaaaacc ttgtatgcat ttcatttaat gttttttgag    2580
attaaaagct taaacaagaa tctctagttt tctttcttgc ttttactttt acttccttaa    2640
tactcaagta caattttaat ggagtacttt tttacttttta ctcaagtaag attctagcca    2700 gatacttta cttttaattg agtaaaattt tccctaagta cttgtacttt cacttgagta    2760 aaattttga gtacttttta cacctctg                                       2788
```

<210> SEQ ID NO 2
<211> LENGTH: 200
<212> TYPE: DNA
<213> ORGANISM: Artificial
<220> FEATURE:
<223> OTHER INFORMATION: Synthetic construct of Tol2-L transposon
     sequence

<400> SEQUENCE: 2

```
cagaggtgta aagtacttga gtaatttttac ttgattactg tacttaagta ttatttttgg     60
ggatttttac tttacttgag tacaattaaa aatcaatact ttacttttta cttaattaca    120 ttttttttaga aaaaaagta cttttttactc cttacaattt tatttacagt caaaaagtac    180
```

```
ttatttttg gagatcactt                                                    200

<210> SEQ ID NO 3
<211> LENGTH: 504
<212> TYPE: DNA
<213> ORGANISM: Artificial
<220> FEATURE:
<223> OTHER INFORMATION: Synthetic construct of Tol2-R transposon
      sequence

<400> SEQUENCE: 3
ctgctcacgt tcctgctat ttgcagcctc tctatcaaga ctaatacacc tcttcccgca         60
tcggctgcct gtgagaggct tttcagcact gcaggattgc ttttcagccc caaaagagct       120
aggcttgaca ctaacaattt tgagaatcag cttctactga agttaaatct gaggttttac       180
aactttgagt agcgtgtact ggcattagat tgtctgtctt atagtttgat aattaaatac       240
aaacagttct aaagcaggat aaaaccttgt atgcatttca tttaatgttt tttgagatta       300
aaagcttaaa caagaatctc tagttttctt tcttgctttt acttttactt ccttaatact       360
caagtacaat tttaatggag tacttttta cttttactca gtaagattc tagccagata        420 cttttacttt taattgagta aaattttccc taagtacttg tactttcact tgagtaaaat      480
ttttgagtac ttttacacc tctg                                               504

<210> SEQ ID NO 4
<211> LENGTH: 2156
<212> TYPE: DNA
<213> ORGANISM: Oryzias latipes
<220> FEATURE:
<221> NAME/KEY: CDS
<222> LOCATION: (85)..(2034)

<400> SEQUENCE: 4
acgtcatgtc acatctatta ccacaatgca cagcaccttg acctggaaat tagggaaatt        60
ataacagtca atcagtggaa gaaa atg gag gaa gta tgt gat tca tca gca           111
                          Met Glu Glu Val Cys Asp Ser Ser Ala
                            1               5 gct gcg agc agc aca gtc caa aat cag cca cag gat caa gag cac ccg         159
Ala Ala Ser Ser Thr Val Gln Asn Gln Pro Gln Asp Gln Glu His Pro
 10              15                  20                  25 tgg ccg tat ctt cgc gaa ttc ttt tct tta agt ggt gta aat aaa gat         207
Trp Pro Tyr Leu Arg Glu Phe Phe Ser Leu Ser Gly Val Asn Lys Asp
                 30                  35                  40 tca ttc aag atg aaa tgt gtc ctc tgt ctc ccg ctt aat aaa gaa ata         255
Ser Phe Lys Met Lys Cys Val Leu Cys Leu Pro Leu Asn Lys Glu Ile
             45                  50                  55 tcg gcc ttc aaa agt tcg cca tca aac cta agg aag cat att gag aga         303
Ser Ala Phe Lys Ser Ser Pro Ser Asn Leu Arg Lys His Ile Glu Arg
         60                  65                  70 atg cac cca aat tac ctc aaa aac tac tct aaa ttg aca gca cag aag         351
Met His Pro Asn Tyr Leu Lys Asn Tyr Ser Lys Leu Thr Ala Gln Lys
     75                  80                  85 aga aag atc ggg acc tcc acc cat gct tcc agc agt aag caa ctg aaa         399
Arg Lys Ile Gly Thr Ser Thr His Ala Ser Ser Ser Lys Gln Leu Lys
 90                  95                 100                 105 gtt gac tca gtt ttc cca gtc aaa cat gtg tct cca gtc act gtg aac         447
Val Asp Ser Val Phe Pro Val Lys His Val Ser Pro Val Thr Val Asn
                110                 115                 120 aaa gct ata tta agg tac atc att caa gga ctt cat cct ttc agc act         495
Lys Ala Ile Leu Arg Tyr Ile Ile Gln Gly Leu His Pro Phe Ser Thr
            125                 130                 135
```

```
gtt gat ctg cca tca ttt aaa gag ctg att agt aca ctg cag cct ggc      543
Val Asp Leu Pro Ser Phe Lys Glu Leu Ile Ser Thr Leu Gln Pro Gly
        140             145             150 att tct gtc att aca agg cct act tta cgc tcc aag ata gct gaa gct      591
Ile Ser Val Ile Thr Arg Pro Thr Leu Arg Ser Lys Ile Ala Glu Ala
155             160             165 gct ctg atc atg aaa cag aaa gtg act gct gcc atg agt gaa gtt gaa      639
Ala Leu Ile Met Lys Gln Lys Val Thr Ala Ala Met Ser Glu Val Glu
170             175             180             185 tgg att gca acc aca acg gat tgt tgg act gca cgt aga aag tca ttc      687
Trp Ile Ala Thr Thr Thr Asp Cys Trp Thr Ala Arg Arg Lys Ser Phe
            190             195             200 att ggt gta act gct cac tgg atc aac cct gga agt ctt gaa aga cat      735
Ile Gly Val Thr Ala His Trp Ile Asn Pro Gly Ser Leu Glu Arg His
            205             210             215 tcc gct gca ctt gcc tgc aaa aga tta atg ggc tct cat act ttt gag      783
Ser Ala Ala Leu Ala Cys Lys Arg Leu Met Gly Ser His Thr Phe Glu
            220             225             230 gta ctg gcc agt gcc atg aat gat atc cac tca gag tat gaa ata cgt      831
Val Leu Ala Ser Ala Met Asn Asp Ile His Ser Glu Tyr Glu Ile Arg
        235             240             245 gac aag gtt gtt tgc aca acc aca gac agt ggt tcc aac ttt atg aag      879
Asp Lys Val Val Cys Thr Thr Thr Asp Ser Gly Ser Asn Phe Met Lys
250             255             260             265 gct ttc aga gtt ttt ggt gtg gaa aac aat gat atc gag act gag gca      927
Ala Phe Arg Val Phe Gly Val Glu Asn Asn Asp Ile Glu Thr Glu Ala
            270             275             280 aga agg tgt gaa agt gat gac act gat tct gaa ggc tgt ggt gag gga      975
Arg Arg Cys Glu Ser Asp Asp Thr Asp Ser Glu Gly Cys Gly Glu Gly
            285             290             295 agt gat ggt gtg gaa ttc caa gat gcc tca cga gtc ctg gac caa gac     1023
Ser Asp Gly Val Glu Phe Gln Asp Ala Ser Arg Val Leu Asp Gln Asp
        300             305             310 gat ggc ttc gaa ttc cag cta cca aaa cat caa aag tgt gcc tgt cac     1071
Asp Gly Phe Glu Phe Gln Leu Pro Lys His Gln Lys Cys Ala Cys His
315             320             325 tta ctt aac cta gtc tca agc gtt gat gcc caa aaa gct ctc tca aat     1119
Leu Leu Asn Leu Val Ser Ser Val Asp Ala Gln Lys Ala Leu Ser Asn
330             335             340             345 gaa cac tac aag aaa ctc tac aga tct gtc ttt ggc aaa tgc caa gct     1167
Glu His Tyr Lys Lys Leu Tyr Arg Ser Val Phe Gly Lys Cys Gln Ala
            350             355             360 tta tgg aat aaa agc agc cga tcg gct cta gca gct gaa gct gtt gaa     1215
Leu Trp Asn Lys Ser Ser Arg Ser Ala Leu Ala Ala Glu Ala Val Glu
            365             370             375 tca gaa agc cgg ctt cag ctt tta agg cca aac caa acg cgg tgg aat     1263
Ser Glu Ser Arg Leu Gln Leu Leu Arg Pro Asn Gln Thr Arg Trp Asn
        380             385             390 tca act ttt atg gct gtt gac aga att ctt caa att tgc aaa gaa gca     1311
Ser Thr Phe Met Ala Val Asp Arg Ile Leu Gln Ile Cys Lys Glu Ala
        395             400             405 gga gaa ggc gca ctt cgg aat ata tgc acc tct ctt gag gtt cca atg     1359
Gly Glu Gly Ala Leu Arg Asn Ile Cys Thr Ser Leu Glu Val Pro Met
410             415             420             425 ttt aat cca gca gaa atg ctg ttc ttg aca gag tgg gcc aac aca atg     1407
Phe Asn Pro Ala Glu Met Leu Phe Leu Thr Glu Trp Ala Asn Thr Met
            430             435             440 cgt cca gtt gca aaa gta ctc gac atc ttg caa gcg gaa acg aat aca     1455
Arg Pro Val Ala Lys Val Leu Asp Ile Leu Gln Ala Glu Thr Asn Thr
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 445 |     |     |     |     | 450 |     |     |     |     | 455 |     |     |     |      |
| cag | ctg | ggg | tgg | ctg | ctg | cct | agt | gtc | cat | cag | tta | agc | ttg | aaa | ctt | 1503 |
| Gln | Leu | Gly | Trp | Leu | Leu | Pro | Ser | Val | His | Gln | Leu | Ser | Leu | Lys | Leu |      |
|     |     | 460 |     |     |     |     | 465 |     |     |     |     | 470 |     |     |     |      |
| cag | cga | ctc | cac | cat | tct | ctc | agg | tac | tgt | gac | cca | ctt | gtg | gat | gcc | 1551 |
| Gln | Arg | Leu | His | His | Ser | Leu | Arg | Tyr | Cys | Asp | Pro | Leu | Val | Asp | Ala |      |
|     | 475 |     |     |     |     | 480 |     |     |     |     | 485 |     |     |     |     |      |
| cta | caa | caa | gga | atc | caa | aca | cga | ttc | aag | cat | atg | ttt | gaa | gat | cct | 1599 |
| Leu | Gln | Gln | Gly | Ile | Gln | Thr | Arg | Phe | Lys | His | Met | Phe | Glu | Asp | Pro |      |
| 490 |     |     |     |     | 495 |     |     |     |     | 500 |     |     |     |     | 505 |      |
| gag | atc | ata | gca | gct | gcc | atc | ctt | ctc | cct | aaa | ttt | cgg | acc | tct | tgg | 1647 |
| Glu | Ile | Ile | Ala | Ala | Ala | Ile | Leu | Leu | Pro | Lys | Phe | Arg | Thr | Ser | Trp |      |
|     |     |     |     | 510 |     |     |     |     | 515 |     |     |     |     | 520 |     |      |
| aca | aat | gat | gaa | acc | atc | ata | aaa | cga | ggc | atg | gac | tac | atc | aga | gtg | 1695 |
| Thr | Asn | Asp | Glu | Thr | Ile | Ile | Lys | Arg | Gly | Met | Asp | Tyr | Ile | Arg | Val |      |
|     |     |     | 525 |     |     |     |     | 530 |     |     |     |     | 535 |     |     |      |
| cat | ctg | gag | cct | ttg | gac | cac | aag | aag | gaa | ttg | gcc | aac | agt | tca | tct | 1743 |
| His | Leu | Glu | Pro | Leu | Asp | His | Lys | Lys | Glu | Leu | Ala | Asn | Ser | Ser | Ser |      |
|     |     |     | 540 |     |     |     |     | 545 |     |     |     |     | 550 |     |     |      |
| gat | gat | gaa | gat | ttt | ttc | gct | tct | ttg | aaa | ccg | aca | aca | cat | gaa | gcc | 1791 |
| Asp | Asp | Glu | Asp | Phe | Phe | Ala | Ser | Leu | Lys | Pro | Thr | Thr | His | Glu | Ala |      |
| 555 |     |     |     |     | 560 |     |     |     |     | 565 |     |     |     |     |     |      |
| agc | aaa | gag | ttg | gat | gga | tat | ctg | gcc | tgt | gtt | tca | gac | acc | agg | gag | 1839 |
| Ser | Lys | Glu | Leu | Asp | Gly | Tyr | Leu | Ala | Cys | Val | Ser | Asp | Thr | Arg | Glu |      |
| 570 |     |     |     |     | 575 |     |     |     |     | 580 |     |     |     |     | 585 |      |
| tct | ctg | ctc | acg | ttt | cct | gct | att | tgc | agc | ctc | tct | atc | aag | act | aat | 1887 |
| Ser | Leu | Leu | Thr | Phe | Pro | Ala | Ile | Cys | Ser | Leu | Ser | Ile | Lys | Thr | Asn |      |
|     |     |     |     | 590 |     |     |     |     | 595 |     |     |     |     | 600 |     |      |
| aca | cct | ctt | ccc | gca | tcg | gct | gcc | tgt | gag | agg | ctt | ttc | agc | act | gca | 1935 |
| Thr | Pro | Leu | Pro | Ala | Ser | Ala | Ala | Cys | Glu | Arg | Leu | Phe | Ser | Thr | Ala |      |
|     |     |     | 605 |     |     |     |     | 610 |     |     |     |     | 615 |     |     |      |
| gga | ttg | ctt | ttc | agc | ccc | aaa | aga | gct | agg | ctt | gac | act | aac | aat | ttt | 1983 |
| Gly | Leu | Leu | Phe | Ser | Pro | Lys | Arg | Ala | Arg | Leu | Asp | Thr | Asn | Asn | Phe |      |
|     |     | 620 |     |     |     |     | 625 |     |     |     |     | 630 |     |     |     |      |
| gag | aat | cag | ctt | cta | ctg | aag | tta | aat | ctg | agg | ttt | tac | aac | ttt | gag | 2031 |
| Glu | Asn | Gln | Leu | Leu | Leu | Lys | Leu | Asn | Leu | Arg | Phe | Tyr | Asn | Phe | Glu |      |
| 635 |     |     |     |     | 640 |     |     |     |     | 645 |     |     |     |     |     |      |
| tag | cgtgtactgg | cattagattg | tctgtcttat | agtttgataa | ttaaatacaa |     |     |     |     |     |     |     |     |     |     | 2084 |
| acagttctaa | agcaggataa | aaccttgtat | gcatttcatt | taatgttttt | tgagattaaa |     |     |     |     |     |     |     |     |     |     | 2144 |
| agcttaaaca | ag |     |     |     |     |     |     |     |     |     |     |     |     |     |     | 2156 |

<210> SEQ ID NO 5
<211> LENGTH: 649
<212> TYPE: PRT
<213> ORGANISM: Oryzias latipes

<400> SEQUENCE: 5

Met Glu Glu Val Cys Asp Ser Ser Ala Ala Ser Ser Thr Val Gln
1               5                   10                  15

Asn Gln Pro Gln Asp Gln Glu His Pro Trp Pro Tyr Leu Arg Glu Phe
                20                  25                  30

Phe Ser Leu Ser Gly Val Asn Lys Asp Ser Phe Lys Met Lys Cys Val
            35                  40                  45

Leu Cys Leu Pro Leu Asn Lys Glu Ile Ser Ala Phe Lys Ser Ser Pro
        50                  55                  60

Ser Asn Leu Arg Lys His Ile Glu Arg Met His Pro Asn Tyr Leu Lys
65                  70                  75                  80

-continued

```
Asn Tyr Ser Lys Leu Thr Ala Gln Lys Arg Lys Ile Gly Thr Ser Thr
                85                  90                  95

His Ala Ser Ser Lys Gln Leu Lys Val Asp Ser Val Phe Pro Val
        100                 105                 110

Lys His Val Ser Pro Val Thr Val Asn Lys Ala Ile Leu Arg Tyr Ile
            115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
```

```
                500              505              510
Leu Leu Pro Lys Phe Arg Thr Ser Trp Thr Asn Asp Glu Thr Ile Ile
            515              520              525

Lys Arg Gly Met Asp Tyr Ile Arg Val His Leu Glu Pro Leu Asp His
            530              535              540

Lys Lys Glu Leu Ala Asn Ser Ser Ser Asp Asp Glu Asp Phe Phe Ala
545             550              555              560

Ser Leu Lys Pro Thr Thr His Glu Ala Ser Lys Glu Leu Asp Gly Tyr
                565              570              575

Leu Ala Cys Val Ser Asp Thr Arg Glu Ser Leu Leu Thr Phe Pro Ala
            580              585              590

Ile Cys Ser Leu Ser Ile Lys Thr Asn Thr Pro Leu Pro Ala Ser Ala
            595              600              605

Ala Cys Glu Arg Leu Phe Ser Thr Ala Gly Leu Leu Phe Ser Pro Lys
            610              615              620

Arg Ala Arg Leu Asp Thr Asn Asn Phe Glu Asn Gln Leu Leu Leu Lys
625             630              635              640

Leu Asn Leu Arg Phe Tyr Asn Phe Glu
                645
```

<210> SEQ ID NO 6
<211> LENGTH: 4682
<212> TYPE: DNA
<213> ORGANISM: Oryzias latipes

<400> SEQUENCE: 6

```
cagaggtgta aagtacttga gtaattttac ttgattactg tacttaagta ttattttggg      60
ggattttac tttacttgag tacaattaaa aatcaatact tttactttta cttaattaca     120
ttttttaga aaaaaagta cttttactc cttacaattt tatttacagt caaaaagtac       180
ttattttttg gagatcactt cattctattt tcccttgcta ttaccaaacc aattgaattg    240
cgctgatgcc cagtttaatt taaatgttat ttattctgcc tatgaaaatc gttttcacat   300
tatatgaaat tggtcagaca tgttcattgg tcctttggaa gtgacgtcat gtcacatcta   360
ttaccacaat gcacagcacc ttgacctgga aattagggaa attataacag tcaatcagtg   420
gaagaaaatg gaggaagtat gtgattcatc agcagctgcg agcagcacag tccaaaatca   480
gccacaggat caagagcacc cgtggccgta tcttcgcgaa ttcttttctt taagtggtgt   540
aaataaagat tcattcaaga tgaaatgtgt cctctgtctc ccgcttaata agaaatatc    600
ggccttcaaa agttcgccat caaacctaag gaagcatatt gaggtaagta cattaagtat  660
tttgttttac tgatagtttt tttttttttt tttttttttt ttttgggtg tgcatgtttt    720
gacgttgatg gcgcgccttt tatatgtgta gtaggcctat tttcactaat gcatgcgatt   780
gacaatataa ggctcacgta ataaaatgct aaaatgcatt tgtaattggt aacgttaggt   840
ccacgggaaa tttggcgcct attgcagctt tgaataatca ttatcattcc gtgctctcat   900
tgtgtttgaa ttcatgcaaa acacaagaaa accaagcgag aaatttttt ccaaacatgt   960
tgtattgtca aaacggtaac actttacaat gaggttgatt agttcatgta ttaactaaca  1020
ttaaataacc atgagcaata catttgttac tgtatctgtt aatctttgtt aacgttagtt  1080
aatagaaata cagatgttca ttgtttgttc atgttagttc acagtgcatt aactaatgtt  1140
aacaagatat aaagtattag taatgttga aattaacatg tatacgtgca gttcattatt   1200
agttcatgtt aactaatgta gttaactaac gaaccttatt gtaaaagtgt taccatcaaa   1260
```

```
actaatgtaa tgaaatcaat tcaccctgtc atgtcagcct tacagtcctg tgttttgtc    1320 aatataatca gaaataaaat taatgtttga ttgtcactaa atgctactgt atttctaaaa   1380
tcaacaagta tttaacatta taaagtgtgc aattggctgc aaatgtcagt tttattaaag   1440
ggttagttca cccaaaaatg aaaataatgt cattaatgac tcgccctcat gtcgttccaa   1500
gcccgtaaga cctccgttca tcttcagaac acagtttaag atattttaga tttagtccga   1560
gagctttctg tgcctccatt gagaatgtat gtacggtata ctgtccatgt ccagaaaggt   1620
aataaaaaca tcaaagtagt ccatgtgaca tcagtgggtt agttagaatt ttttgaagca   1680
tcgaatacat tttggtccaa aaataacaaa acctacgact ttattcggca ttgtattctc   1740
ttccgggtct gttgtcaatc cgcgttcacg acttcgcagt gacgctacaa tgctgaataa   1800
agtcgtaggt tttgttattt ttggaccaaa atgtattttc gatgcttcaa ataattctac   1860
ctaacccact gatgtcacat ggactacttt gatgttttta ttaccttttct ggacatggac   1920 agtataccgt acatacattt tcagtggagg gacagaaagc tctcggacta aatctaaaat   1980
atcttaaact gtgttccgaa gatgaacgga ggtgttacgg gcttggaacg acatgagggt   2040
gagtcattaa tgcatctctt tcatttttgg gtgaactaac cctttaatgc tgtaatcaga   2100
gagtgtatgt gtaattgtta catttattgc atacaatata aatatttatt tgttgttttt   2160
acagagaatg cacccaaatt acctcaaaaa ctactctaaa ttgacagcac agaagagaaa   2220
gatcgggacc tccacccatg cttccagcag taagcaactg aaagttgact cagttttccc   2280
agtcaaacat gtgtctccag tcactgtgaa caaagctata ttaaggtaca tcattcaagg   2340
acttcatcct ttcagcactg ttgatctgcc atcatttaaa gagctgatta gtacactgca   2400
gcctggcatt tctgtcatta caaggcctac tttacgctcc aagatagctg aagctgctct   2460
gatcatgaaa cagaaagtga ctgctgccat gagtgaagtt gaatggattg caaccacaac   2520
ggattgttgg actgcacgta gaaagtcatt cattggtgta actgctcact ggatcaaccc   2580
tggaagtctt gaaagacatt ccgctgcact tgcctgcaaa agattaatgg gctctcatac   2640
ttttgaggta ctggccagtg ccatgaatga tatccactca gagtatgaaa tacgtgacaa   2700
ggttgtttgc acaaccacag acagtggttc caactttatg aaggcttca gagttttgg    2760 tgtggaaaac aatgatatcg agactgaggc aagaaggtgt gaaagtgatg acactgattc   2820
tgaaggctgt ggtgagggaa gtgatggtgt ggaattccaa gatgcctcac gagtcctgga   2880
ccaagacgat ggcttcgaat ccagctacc aaaacatcaa aagtgtgcct gtcacttact    2940
taacctagtc tcaagcgttg atgcccaaaa agctctctca aatgaacact acaagaaact   3000
ctacagatct gtctttggca aatgccaagc tttatggaat aaaagcagcc gatcggctct   3060
agcagctgaa gctgttgaat cagaaagccg gcttcagctt ttaaggccaa accaaacgcg   3120
gtggaattca acttttatgg ctgttgacag aattcttcaa atttgcaaag aagcaggaga   3180
aggcgcactt cggaatatat gcacctctct tgaggttcca atgtaagtgt ttttcccctc   3240
tatcgatgta aacaaatgtg ggttgttttt gtttaatact ctttgattat gctgatttct   3300
cctgtaggtt taatccagca gaaatgctgt tcttgacaga gtgggccaac acaatgcgtc   3360
cagttgcaaa agtactcgac atcttgcaag cggaaacgaa tacacagctg ggtggctgc    3420 tgcctagtgt ccatcagtta agcttgaaac ttcagcgact ccaccattct ctcaggtact   3480
gtgacccact tgtggatgcc ctacaacaag gaatccaaac acgattcaag catatgtttg   3540
aagatcctga gatcatagca gctgccatcc ttctccctaa atttcggacc tcttggacaa   3600
atgatgaaac catcataaaa cgaggtaaat gaatgcaagc aacatacact tgacgaattc   3660
```

```
taatctgggc aacctttgag ccataccaaa attattcttt tatttattta tttttgcact    3720
ttttaggaat gttatatccc atctttggct gtgatctcaa tatgaatatt gatgtaaagt    3780
attcttgcag caggttgtag ttatccctca gtgtttcttg aaaccaaact catatgtatc    3840
atatgtggtt tggaaatgca gttagatttt atgctaaaat aagggatttg catgatttta    3900
gatgtagatg actgcacgta aatgtagtta atgacaaaat ccataaaatt tgttcccagt    3960
cagaagcccc tcaaccaaac ttttctttgt gtctgctcac tgtgcttgta ggcatggact    4020
acatcagagt gcatctggag cctttggacc acaagaagga attggccaac agttcatctg    4080
atgatgaaga ttttttcgct tctttgaaac cgacaacaca tgaagccagc aaagagttgg    4140
atggatatct ggcctgtgtt tcagacacca gggagtctct gctcacgttt cctgctattt    4200
gcagcctctc tatcaagact aatacacctc ttcccgcatc ggctgcctgt gagaggcttt    4260
tcagcactgc aggattgctt ttcagcccca aaagagctag gcttgacact aacaattttg    4320
agaatcagct tctactgaag ttaaatctga ggttttacaa ctttgagtag cgtgtactgg    4380
cattagattg tctgtcttat agtttgataa ttaaatacaa acagttctaa agcaggataa    4440
aaccttgtat gcatttcatt taatgttttt tgagattaaa agcttaaaca agaatctcta    4500
gttttctttc ttgcttttac ttttacttcc ttaatactca agtacaattt taatggagta    4560
cttttttact tttactcaag taagattcta gccagatact tttactttta attgagtaaa    4620
attttcccta agtacttgta ctttcacttg agtaaaattt ttgagtactt tttacacctc    4680
tg                                                                   4682

<210> SEQ ID NO 7
<211> LENGTH: 321
<212> TYPE: DNA
<213> ORGANISM: Artificial
<220> FEATURE:
<223> OTHER INFORMATION: Synthetic construct of Cycloheximide resistant
      gene
<220> FEATURE:
<221> NAME/KEY: CDS
<222> LOCATION: (1)..(321)

<400> SEQUENCE: 7 atg gtc aac gta cct aaa acc cga aga acc ttc tgt aag aag tgt ggc     48
Met Val Asn Val Pro Lys Thr Arg Arg Thr Phe Cys Lys Lys Cys Gly
1               5                   10                  15 aag cat cag cct cac aaa gtg aca cag tat aag aag ggc aag gat tct     96
Lys His Gln Pro His Lys Val Thr Gln Tyr Lys Lys Gly Lys Asp Ser
            20                  25                  30 ttg tat gcc cag gga agg agg cgc tat gat cgg aag cag agt ggc tat    144
Leu Tyr Ala Gln Gly Arg Arg Arg Tyr Asp Arg Lys Gln Ser Gly Tyr
        35                  40                  45 ggt ggg cag aca aag caa att ttc cgg aag aag gct aag acc aca aag    192
Gly Gly Gln Thr Lys Gln Ile Phe Arg Lys Lys Ala Lys Thr Thr Lys
    50                  55                  60 aag att gtg cta agg ctg gaa tgt gtt gag cct aac tgc aga tcc aag    240
Lys Ile Val Leu Arg Leu Glu Cys Val Glu Pro Asn Cys Arg Ser Lys
65                  70                  75                  80 agg atg ctg gcc att aag aga tgc aag cat ttt gaa ctg gga gga gat    288
Arg Met Leu Ala Ile Lys Arg Cys Lys His Phe Glu Leu Gly Gly Asp
                85                  90                  95 aag aag aga aag ggc caa gtg atc cag ttc taa                        321
Lys Lys Arg Lys Gly Gln Val Ile Gln Phe
                100                 105
```

```
<210> SEQ ID NO 8
<211> LENGTH: 106
<212> TYPE: PRT
<213> ORGANISM: Artificial
<220> FEATURE:
<223> OTHER INFORMATION: Synthetic Construct

<400> SEQUENCE: 8

Met Val Asn Val Pro Lys Thr Arg Arg Thr Phe Cys Lys Lys Cys Gly
1               5                   10                  15

Lys His Gln Pro His Lys Val Thr Gln Tyr Lys Lys Gly Lys Asp Ser
            20                  25                  30

Leu Tyr Ala Gln Gly Arg Arg Arg Tyr Asp Arg Lys Gln Ser Gly Tyr
        35                  40                  45

Gly Gly Gln Thr Lys Gln Ile Phe Arg Lys Lys Ala Lys Thr Thr Lys
    50                  55                  60

Lys Ile Val Leu Arg Leu Glu Cys Val Glu Pro Asn Cys Arg Ser Lys
65                  70                  75                  80

Arg Met Leu Ala Ile Lys Arg Cys Lys His Phe Glu Leu Gly Gly Asp
                85                  90                  95

Lys Lys Arg Lys Gly Gln Val Ile Gln Phe
            100                 105

<210> SEQ ID NO 9
<211> LENGTH: 1404
<212> TYPE: DNA
<213> ORGANISM: Artificial
<220> FEATURE:
<223> OTHER INFORMATION: Synthetic construct of M2Z3 Heavy chain
<220> FEATURE:
<221> NAME/KEY: CDS
<222> LOCATION: (1)..(1404)

<400> SEQUENCE: 9 atg gac tgg acc tgg agc atc ctt ttc ttg gtg gca gca gca aca ggt      48
Met Asp Trp Thr Trp Ser Ile Leu Phe Leu Val Ala Ala Ala Thr Gly
1               5                   10                  15 gcc cac tcc cag gtt cag ctg gtg cag tct gga gct gag gtg aag aag      96
Ala His Ser Gln Val Gln Leu Val Gln Ser Gly Ala Glu Val Lys Lys
            20                  25                  30 cct ggg gcc tca gtg aag gtc tcc tgc aag gct tct ggt tac acc ttt     144
Pro Gly Ala Ser Val Lys Val Ser Cys Lys Ala Ser Gly Tyr Thr Phe
        35                  40                  45 acc agc tat ggt atc agc tgg gtg cga cag gcc cct gga caa ggg ctt     192
Thr Ser Tyr Gly Ile Ser Trp Val Arg Gln Ala Pro Gly Gln Gly Leu
    50                  55                  60 gag tgg atg gga tgg atc agc gct tac aat ggt aac aca aac tat gca     240
Glu Trp Met Gly Trp Ile Ser Ala Tyr Asn Gly Asn Thr Asn Tyr Ala
65                  70                  75                  80 cag aag ctc cag ggc aga gtc acc atg acc aca gac aca tcc acg agc     288
Gln Lys Leu Gln Gly Arg Val Thr Met Thr Thr Asp Thr Ser Thr Ser
                85                  90                  95 aca gcc tac atg gag ctg agg agc ctg aga tct gac gac acg gcc gtg     336
Thr Ala Tyr Met Glu Leu Arg Ser Leu Arg Ser Asp Asp Thr Ala Val
            100                 105                 110 tat tac tgt gcg agg gca gca gct ggc gga tac ttc cag cac tgg ggc     384
Tyr Tyr Cys Ala Arg Ala Ala Ala Gly Gly Tyr Phe Gln His Trp Gly
        115                 120                 125 cag ggc acc ctg gtc acc gtc tcc tca gct agc acc aag ggc cca tcg     432
Gln Gly Thr Leu Val Thr Val Ser Ser Ala Ser Thr Lys Gly Pro Ser
    130                 135                 140
```

-continued

| | |
|---|---|
| gtc ttc ccc ctg gca ccc tcc tcc aag agc acc tct ggg ggc aca gcg<br>Val Phe Pro Leu Ala Pro Ser Ser Lys Ser Thr Ser Gly Gly Thr Ala<br>145                    150                   155                   160 | 480 |
| gcc ctg ggc tgc ctg gtc aag gac tac ttc ccc gaa ccg gtg acg gtg<br>Ala Leu Gly Cys Leu Val Lys Asp Tyr Phe Pro Glu Pro Val Thr Val<br>                    165                   170                   175 | 528 |
| tcg tgg aac tca ggc gcc ctg acc agc ggc gtg cac acc ttc ccg gct<br>Ser Trp Asn Ser Gly Ala Leu Thr Ser Gly Val His Thr Phe Pro Ala<br>         180                   185                   190 | 576 |
| gtc cta cag tcc tca gga ctc tac tcc ctc agc agc gtg gtg acc gtg<br>Val Leu Gln Ser Ser Gly Leu Tyr Ser Leu Ser Ser Val Val Thr Val<br>        195                   200                   205 | 624 |
| ccc tcc agc agc ttg ggc acc cag acc tac atc tgc aac gtg aat cac<br>Pro Ser Ser Ser Leu Gly Thr Gln Thr Tyr Ile Cys Asn Val Asn His<br>210                    215                   220 | 672 |
| aag ccc agc aac acc aag gtg gac aag aaa gtt gag ccc aaa tct tgt<br>Lys Pro Ser Asn Thr Lys Val Asp Lys Lys Val Glu Pro Lys Ser Cys<br>225                    230                   235                   240 | 720 |
| gac aaa act cac aca tgc cca ccg tgc cca gca cct gaa ctc ctg ggg<br>Asp Lys Thr His Thr Cys Pro Pro Cys Pro Ala Pro Glu Leu Leu Gly<br>                    245                   250                   255 | 768 |
| gga ccg tca gtc ttc ctc ttc ccc cca aaa ccc aag gac acc ctc atg<br>Gly Pro Ser Val Phe Leu Phe Pro Pro Lys Pro Lys Asp Thr Leu Met<br>         260                   265                   270 | 816 |
| atc tcc cgg acc cct gag gtc aca tgc gtg gtg gtg gac gtg agc cac<br>Ile Ser Arg Thr Pro Glu Val Thr Cys Val Val Val Asp Val Ser His<br>        275                   280                   285 | 864 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>290                    295                   300 | 912 |
| cat aat gcc aag aca aag ccg cgg gag gag cag tac aac agc acg tac<br>His Asn Ala Lys Thr Lys Pro Arg Glu Glu Gln Tyr Asn Ser Thr Tyr<br>305                    310                   315                   320 | 960 |
| cgt gtg gtc agc gtc ctc acc gtc ctg cac cag gac tgg ctg aat ggc<br>Arg Val Val Ser Val Leu Thr Val Leu His Gln Asp Trp Leu Asn Gly<br>                    325                   330                   335 | 1008 |
| aag gag tac aag tgc aag gtc tcc aac aaa gcc ctc cca gcc ccc atc<br>Lys Glu Tyr Lys Cys Lys Val Ser Asn Lys Ala Leu Pro Ala Pro Ile<br>         340                   345                   350 | 1056 |
| gag aaa acc atc tcc aaa gcc aaa ggg cag ccc cga gaa cca cag gtg<br>Glu Lys Thr Ile Ser Lys Ala Lys Gly Gln Pro Arg Glu Pro Gln Val<br>        355                   360                   365 | 1104 |
| tac acc ctg ccc cca tcc cgg gat gag ctg acc aag aac cag gtc agc<br>Tyr Thr Leu Pro Pro Ser Arg Asp Glu Leu Thr Lys Asn Gln Val Ser<br>370                    375                   380 | 1152 |
| ctg acc tgc ctg gtc aaa ggc ttc tat ccc agc gac atc gcc gtg gag<br>Leu Thr Cys Leu Val Lys Gly Phe Tyr Pro Ser Asp Ile Ala Val Glu<br>385                    390                   395                   400 | 1200 |
| tgg gag agc aat ggg cag ccg gag aac aac tac aag acc acg cct ccc<br>Trp Glu Ser Asn Gly Gln Pro Glu Asn Asn Tyr Lys Thr Thr Pro Pro<br>                    405                   410                   415 | 1248 |
| gtg ctg gac tcc gac ggc tcc ttc ttc ctc tac agc aag ctc acc gtg<br>Val Leu Asp Ser Asp Gly Ser Phe Phe Leu Tyr Ser Lys Leu Thr Val<br>         420                   425                   430 | 1296 |
| gac aag agc agg tgg cag cag ggg aac gtc ttc tca tgc tcc gtg atg<br>Asp Lys Ser Arg Trp Gln Gln Gly Asn Val Phe Ser Cys Ser Val Met<br>        435                   440                   445 | 1344 |
| cat gag gct ctg cac aac cac tac acg cag aag agc ctc tcc ctg tct<br>His Glu Ala Leu His Asn His Tyr Thr Gln Lys Ser Leu Ser Leu Ser | 1392 |

```
            450                 455                 460
ccg ggt aaa tga                                                        1404
Pro Gly Lys
465

<210> SEQ ID NO 10
<211> LENGTH: 467
<212> TYPE: PRT
<213> ORGANISM: Artificial
<220> FEATURE:
<223> OTHER INFORMATION: Synthetic Construct

<400> SEQUENCE: 10

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ala Ala Gly Gly Tyr Phe Gln His Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335
```

-continued

```
Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 11
<211> LENGTH: 708
<212> TYPE: DNA
<213> ORGANISM: Artificial
<220> FEATURE:
<223> OTHER INFORMATION: Synthetic construct of M2Z3 Light chian
<220> FEATURE:
<221> NAME/KEY: CDS
<222> LOCATION: (1)..(708)

<400> SEQUENCE: 11 atg gcc agc ttc cct ctc ctc ctc acc ctc ctc act cac tgt gca ggg    48
Met Ala Ser Phe Pro Leu Leu Leu Thr Leu Leu Thr His Cys Ala Gly
1               5                   10                  15 tcc tgg gcc cag tct gtg ctg act cag cca ccc tca gcg tct ggg acc    96
Ser Trp Ala Gln Ser Val Leu Thr Gln Pro Pro Ser Ala Ser Gly Thr
            20                  25                  30 ccc ggg cag agg gtc acc atc tct tgt tct gga agc aac tcc aac atc   144
Pro Gly Gln Arg Val Thr Ile Ser Cys Ser Gly Ser Asn Ser Asn Ile
        35                  40                  45 gga agt aaa act gta aac tgg tac cag cag ctc cca gga acg gcc ccc   192
Gly Ser Lys Thr Val Asn Trp Tyr Gln Gln Leu Pro Gly Thr Ala Pro
    50                  55                  60 aaa ctc ctc atc tct agt aat aat cag cgg ccc tca ggg gtc cct gac   240
Lys Leu Leu Ile Ser Ser Asn Asn Gln Arg Pro Ser Gly Val Pro Asp
65                  70                  75                  80 cga ttc tct ggc tcc aag tct ggc acc tca gcc tcc ctg gcc atc agt   288
Arg Phe Ser Gly Ser Lys Ser Gly Thr Ser Ala Ser Leu Ala Ile Ser
                85                  90                  95 ggg ctc cag tct gag gat gag gct gat tat tac tgt gca gca tgg gat   336
Gly Leu Gln Ser Glu Asp Glu Ala Asp Tyr Tyr Cys Ala Ala Trp Asp
            100                 105                 110 gac agc ctg aat ggt gtg gta ttc ggc gga ggg acc aag ctg acc gtc   384
Asp Ser Leu Asn Gly Val Val Phe Gly Gly Gly Thr Lys Leu Thr Val
        115                 120                 125 cta ggt cag ccc aag gct gcc ccc tcg gtc act ctg ttc cca ccc tcc   432
Leu Gly Gln Pro Lys Ala Ala Pro Ser Val Thr Leu Phe Pro Pro Ser
    130                 135                 140 tct gag gag ctt caa gcc aac aag gcc aca ctg gtg tgt ctc ata agt   480
Ser Glu Glu Leu Gln Ala Asn Lys Ala Thr Leu Val Cys Leu Ile Ser
145                 150                 155                 160
```

```
gac ttc tac ccg gga gcc gtg aca gtg gcc tgg aag gca gat agc agc     528
Asp Phe Tyr Pro Gly Ala Val Thr Val Ala Trp Lys Ala Asp Ser Ser
            165                 170                 175 ccc gtc aag gcg gga gtg gag acc acc aca ccc tcc aaa caa agc aac     576
Pro Val Lys Ala Gly Val Glu Thr Thr Thr Pro Ser Lys Gln Ser Asn
        180                 185                 190 aac aag tac gcg gcc agc agc tac ctg agc ctg acg cct gag cag tgg     624
Asn Lys Tyr Ala Ala Ser Ser Tyr Leu Ser Leu Thr Pro Glu Gln Trp
    195                 200                 205 aag tcc cac aaa agc tac agc tgc cag gtc acg cat gaa ggg agc acc     672
Lys Ser His Lys Ser Tyr Ser Cys Gln Val Thr His Glu Gly Ser Thr
210                 215                 220 gtg gag aag aca gtg gcc cct aca gaa tgt tca tag                     708
Val Glu Lys Thr Val Ala Pro Thr Glu Cys Ser
225                 230                 235

<210> SEQ ID NO 12
<211> LENGTH: 235
<212> TYPE: PRT
<213> ORGANISM: Artificial
<220> FEATURE:
<223> OTHER INFORMATION: Synthetic Construct

<400> SEQUENCE: 12

Met Ala Ser Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Asn Ser Asn Ile
        35                  40                  45

Gly Ser Lys Thr Val Asn Trp Tyr Gln Gln Leu Pro Gly Thr Ala Pro
    50                  55                  60

Lys Leu Leu Ile Ser Ser Asn Asn Gln Arg Pro Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Gln Ser Glu Asp Glu Ala Asp Tyr Tyr Cys Ala Ala Trp Asp
            100                 105                 110

Asp Ser Leu Asn Gly Val Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 13
<211> LENGTH: 1855
```

<212> TYPE: DNA
<213> ORGANISM: artificial
<220> FEATURE:
<223> OTHER INFORMATION: Synthetic construct of nonautologus Tol1 transposon

<400> SEQUENCE: 13

```
cagtagcggt tctaggcacg ggccgtccgg gcggtggcct ggggcggaaa actgaagggg      60
ggcggcaccg gcggctcagc cctttgtaat atattaatat gcaccactat tggtttactt     120
atgtcacagt ttgtaagttt gtaacagcct gaacctggcc gcgccgccgc cctcgccccg     180
cagctgcgct ctcctgtctt tgagaagtag acacaaatgt gtgtgaagaa ggagaaggga     240
gggggcgcgg ggtgagcacg gagcgtcgcc gcgtttgcgc atgcgcaaaa cctggctggc     300
tcatctttca ggggaggcga cggtcgcggg cttgatgaaa aaaataaaag taaaaactgc     360
gactgcgccg tcatgtagcg aatcagcgcc cctggctgta gctgcacgcg ctcctgctgg     420
aaatgtgtga agagggggg ggggggggg gctgcgggga atcagttcaa ttgtgggacg     480
cttccaaatt aagtggctag gtggggacaa gggcgggggt ttgaatctac ttcataaaac     540
cttttatat tataagtcag tcataaggtg acattctata acctacattt taataaaggt     600
ataaaata tattctgctt ttttttgggtt aattttgtgt gaaatgtcca aataaaaaaa     660
atggcaacac aaaacaatgc tgtcactaag gtgacagttg gttcagtcga cggacttgat     720
gccttcttcg tgacgtgagg acattatgc caaacaaacg ccaataaaca tctaaaatat     780
ggaaaagaaa aggtcaaagc catctggtgc ccaatttaga agaaaagaa aagaagaaga     840
ggagaaaaga gataaagaaa agggtaagtc ctcacagctt gatgcatgtt ttttctaaat     900
tctaatgcta cctgccctac aacaacgttg ccgatgaaaa cttttattttg gtcgatgacc     960
aacactgaat taggcccaaa tgttgcaaat agcgtcattt ttttttttt ttttagattt    1020
tattcttaaa aatttgctct gccttaactt gtaacattag ttatgattca tgtgtctgtc    1080
tgctctgctg taacacaaag gttttgttgg gttttgctgt tgtatactag ctcataatgt    1140
taaaaaagct gtgatggtta cacagcatgc tggtgctgcc ataagatgct aatggggcaa    1200
ataatttgag attggtcatt aatttaataa tcatttgtgg cagcctaaac gttttcacaa    1260
tgttttttg acatttaact ggggatttag gggttaattt tgagcctgca tatgaagttt    1320
attttttatt tgtttttacaa atgtgggatt atattttttag ccaatagaat ttccataaat    1380
ctgtaggtag ttttaaaaat gaatattac catttactgc aactctatgg ggacaaaaca    1440
taatgtaaca ggtcataact aaaaatgtgc caatcaaagg attgaagacg gaaaacatga    1500
gttaattttt cttctctgaa gtagagatcg atatagaaca tgacaattta aatttccaat    1560
tcataaatgt ttttaaaata tttatttttat attatttatt taacattgag tttgattcaa    1620
tatttttctta gctaactgta tttttgccat gcttatggtc ttttattttt tgtgttctga    1680
taacttttat aatgcttttc agaattttga catcttttgt atccacttct taattttcaat    1740
gacaataaaa catttcagtt gacgaagaca aacaaagttc tgttgtgact atgggggggg    1800
ggggcgcctg gggatggtct cgcccgggga gtaattcagg gtagaaccgc cactg         1855
```

<210> SEQ ID NO 14
<211> LENGTH: 200
<212> TYPE: DNA
<213> ORGANISM: artificial
<220> FEATURE:
<223> OTHER INFORMATION: Synthetic construct of Tol1-L transposon sequence

<400> SEQUENCE: 14

```
cagtagcggt tctaggcacg ggccgtccgg gcggtggcct ggggcggaaa actgaagggg      60
ggcggcaccg gcggctcagc cctttgtaat atattaatat gcaccactat tggtttactt     120
atgtcacagt ttgtaagttt gtaacagcct gaacctggcc gcgccgccgc cctcgccccg     180
cagctgcgct ctcctgtctt                                                 200
```

<210> SEQ ID NO 15
<211> LENGTH: 505
<212> TYPE: DNA
<213> ORGANISM: artificial
<220> FEATURE:
<223> OTHER INFORMATION: Synthetic construct of Tol1-R transoposon
      sequence

<400> SEQUENCE: 15

```
atatttttag ccaatagaat ttccataaat ctgtaggtag ttttaaaaat gaatatttac      60
catttactgc aactctatgg ggacaaaaca taatgtaaca ggtcataact aaaaatgtgc     120
caatcaaagg attgaagacg gaaaacatga gttaattttt cttctctgaa gtagagatcg     180
atatagaaca tgacaattta aatttccaat tcataaatgt tttaaaaata tttatttat     240
attatttatt taacattgag tttgattcaa tattttctta gctaactgta tttttgccat     300
gcttatggtc ttttattttt tgtgttctga taacttttat aatgcttttc agaattttga     360
catcttttgt atccacttct taatttcaat gacaataaaa catttcagtt gacgaagaca     420
aacaaagttc tgttgtgact atgggggggg ggggcgcctg gggatggtct cgcccgggga     480
gtaattcagg gtagaaccgc cactg                                           505
```

<210> SEQ ID NO 16
<211> LENGTH: 2745
<212> TYPE: DNA
<213> ORGANISM: Oryzias latipes
<220> FEATURE:
<221> NAME/KEY: CDS
<222> LOCATION: (30)..(2585)

<400> SEQUENCE: 16

```
gccaaacaaa cgccaaaaac atctaaaat atg gag aaa aaa agg tca aag cca       53
                                Met Glu Lys Lys Arg Ser Lys Pro
                                  1               5 tct ggt gcc caa ttt aga aag aaa aga aaa gaa gaa gag gag aaa aga      101
Ser Gly Ala Gln Phe Arg Lys Lys Arg Lys Glu Glu Glu Glu Lys Arg
     10                  15                  20 gat aaa gaa aag ggg gca ctt cta aga tat ttt gga tcg tct acc act      149
Asp Lys Glu Lys Gly Ala Leu Leu Arg Tyr Phe Gly Ser Ser Thr Thr
 25                  30                  35                  40 gct caa gat gag aca tct acc tcc ctg cca gct atc tca tca gcc aca      197
Ala Gln Asp Glu Thr Ser Thr Ser Leu Pro Ala Ile Ser Ser Ala Thr
                 45                  50                  55 gtc aca gtc tca ccc cct cag gat gag cta cca tct aca tcc tct gct      245
Val Thr Val Ser Pro Pro Gln Asp Glu Leu Pro Ser Thr Ser Ser Ala
             60                  65                  70 act cat gta gtt cca cag ttg tta cct gag caa agt ttt gat agt gag      293
Thr His Val Val Pro Gln Leu Leu Pro Glu Gln Ser Phe Asp Ser Glu
         75                  80                  85 gct gaa gac gtt gtt cca tct acg tct acc cag ctt gag act tca gaa      341
Ala Glu Asp Val Val Pro Ser Thr Ser Thr Gln Leu Glu Thr Ser Glu
     90                  95                 100 atg cct ggt gat gaa acc cca ctg acc ccg act gct gag gac cag cct      389
```

```
                Met Pro Gly Asp Glu Thr Pro Leu Thr Pro Thr Ala Glu Asp Gln Pro
                105                 110                 115                 120 cta cca act gac cct gca aag tgg ccc tca cct ctg act gac agg ata        437
Leu Pro Thr Asp Pro Ala Lys Trp Pro Ser Pro Leu Thr Asp Arg Ile
                125                 130                 135 cgg atg gag ctg gtt cga aga gga cca agt agc ata cca cct gac ttt        485
Arg Met Glu Leu Val Arg Arg Gly Pro Ser Ser Ile Pro Pro Asp Phe
            140                 145                 150 gtt ttc cca aga aat gac agt gat ggg aga agt tgt cat cac cac tat        533
Val Phe Pro Arg Asn Asp Ser Asp Gly Arg Ser Cys His His His Tyr
            155                 160                 165 ttc agg aag aca cta gta agt ggt gaa aaa ata gca aga act tgg ttg        581
Phe Arg Lys Thr Leu Val Ser Gly Glu Lys Ile Ala Arg Thr Trp Leu
        170                 175                 180 atg tat tca aaa gtg aag aac agc ctc ttt tgc ttt tgt tgc aaa ttg        629
Met Tyr Ser Lys Val Lys Asn Ser Leu Phe Cys Phe Cys Cys Lys Leu
185                 190                 195                 200 ttt tcc aac aaa aac att aat tta aca act tct ggt aca gca aac tgg        677
Phe Ser Asn Lys Asn Ile Asn Leu Thr Thr Ser Gly Thr Ala Asn Trp
            205                 210                 215 aaa cat gca agc aca tac ctc aca gca cac gaa aaa agc cca gaa cac        725
Lys His Ala Ser Thr Tyr Leu Thr Ala His Glu Lys Ser Pro Glu His
            220                 225                 230 ctc aat tgt atg aaa gca tgg aag gaa ctg tca ggg agg atc aga agt        773
Leu Asn Cys Met Lys Ala Trp Lys Glu Leu Ser Gly Arg Ile Arg Ser
        235                 240                 245 ggg aaa aca att gat aag cag gag atg gca ctt ctg gaa gag gag cgg        821
Gly Lys Thr Ile Asp Lys Gln Glu Met Ala Leu Leu Glu Glu Glu Arg
    250                 255                 260 gtg aga tgg aga gca gtg cta acc cgt ctc att gct att gtg cag tca        869
Val Arg Trp Arg Ala Val Leu Thr Arg Leu Ile Ala Ile Val Gln Ser
265                 270                 275                 280 ctg gca gtt cgg aat ttg gct cta agg gga cac aca gaa aca ctg ttc        917
Leu Ala Val Arg Asn Leu Ala Leu Arg Gly His Thr Glu Thr Leu Phe
            285                 290                 295 aca tca tca aat ggg aat ttt ttg aaa gag gtt gaa ctg atg gcc agg        965
Thr Ser Ser Asn Gly Asn Phe Leu Lys Glu Val Glu Leu Met Ala Arg
            300                 305                 310 ttt gat ccc ata atg aaa gat cat ctt aac cgt gta tta aga gga aca       1013
Phe Asp Pro Ile Met Lys Asp His Leu Asn Arg Val Leu Arg Gly Thr
        315                 320                 325 gca agt cac aac agc tac ata ggc cat cat gtg cag aat gaa ctt att       1061
Ala Ser His Asn Ser Tyr Ile Gly His His Val Gln Asn Glu Leu Ile
330                 335                 340 gat ttg ttg agc agc aaa atc cta tcc gct ata gtg gat gac atc aaa       1109
Asp Leu Leu Ser Ser Lys Ile Leu Ser Ala Ile Val Asp Asp Ile Lys
345                 350                 355                 360 aag gca aaa tat ttt tca ata att ctg gac tgc act ctg gat ata agc       1157
Lys Ala Lys Tyr Phe Ser Ile Ile Leu Asp Cys Thr Leu Asp Ile Ser
            365                 370                 375 cac aca gaa cag ttg tca gtt ata att aga gtg gtg tca ctg atg gag       1205
His Thr Glu Gln Leu Ser Val Ile Ile Arg Val Val Ser Leu Met Glu
            380                 385                 390 aag cct cag atc agg gaa cat ttt atg ggg ttt ttg gag gca gag gag       1253
Lys Pro Gln Ile Arg Glu His Phe Met Gly Phe Leu Glu Ala Glu Glu
            395                 400                 405 tcc aca ggc cag cac ttg gca tcc atg atc tta aac aga ctt gag gag       1301
Ser Thr Gly Gln His Leu Ala Ser Met Ile Leu Asn Arg Leu Glu Glu
        410                 415                 420
```

| | |
|---|---|
| tta gga att tct ttt gaa gac tgc aga gga caa tca tat gat aat ggg<br>Leu Gly Ile Ser Phe Glu Asp Cys Arg Gly Gln Ser Tyr Asp Asn Gly<br>425                             430                       435                     440 | 1349 |
| gca aat atg aaa ggc aaa aat aag gga gta caa gcc agg ctc tta gaa<br>Ala Asn Met Lys Gly Lys Asn Lys Gly Val Gln Ala Arg Leu Leu Glu<br>                       445                       450                       455 | 1397 |
| aag aat ccc cgt gct ctg ttt ttg cca tgc ggt gca cac aca ttg aat<br>Lys Asn Pro Arg Ala Leu Phe Leu Pro Cys Gly Ala His Thr Leu Asn<br>            460                     465                       470 | 1445 |
| tta gtt gtg tgt gat gct gct aag aga tct gtt gat gct atg agc tac<br>Leu Val Val Cys Asp Ala Ala Lys Arg Ser Val Asp Ala Met Ser Tyr<br>            475                     480                     485 | 1493 |
| ttt ggt gtc ctg caa aag ctt tac act tta ttt tca gcc tct gcc caa<br>Phe Gly Val Leu Gln Lys Leu Tyr Thr Leu Phe Ser Ala Ser Ala Gln<br>490                             495                       500 | 1541 |
| cga tgg gcc ata ctg aag agt cag gtg agc atc act cta aag tcg tgg<br>Arg Trp Ala Ile Leu Lys Ser Gln Val Ser Ile Thr Leu Lys Ser Trp<br>505                           510                       515             520 | 1589 |
| aca gaa aca agg tgg gag agc aaa atc aaa agc atc gag ccc atg agg<br>Thr Glu Thr Arg Trp Glu Ser Lys Ile Lys Ser Ile Glu Pro Met Arg<br>                   525                       530                       535 | 1637 |
| tac cag gga gct gca gtg aga gag gct tta ata gaa gtg aga gac aag<br>Tyr Gln Gly Ala Ala Val Arg Glu Ala Leu Ile Glu Val Arg Asp Lys<br>               540                       545                       550 | 1685 |
| acc aaa gac cca gtt ata aag gct gag gcc cag tct ttg tct gaa gag<br>Thr Lys Asp Pro Val Ile Lys Ala Glu Ala Gln Ser Leu Ser Glu Glu<br>555                           560                       565 | 1733 |
| gta ggg tcg tac cgc ttc aac atc tgc aca gtc gta tgg cat gac att<br>Val Gly Ser Tyr Arg Phe Asn Ile Cys Thr Val Val Trp His Asp Ile<br>570                           575                       580 | 1781 |
| cta tct aca ata aag cat gtc agc aaa ctc atg cag tct cca aat atg<br>Leu Ser Thr Ile Lys His Val Ser Lys Leu Met Gln Ser Pro Asn Met<br>585                           590                       595             600 | 1829 |
| cat gtg gac cta gct gtg agt ctt ttg aag aag act gaa caa agt ctc<br>His Val Asp Leu Ala Val Ser Leu Leu Lys Lys Thr Glu Gln Ser Leu<br>                     605                       610                       615 | 1877 |
| cag agc tac agg gca aat ggc ttt gtg aat gca cag atg gca gcc aaa<br>Gln Ser Tyr Arg Ala Asn Gly Phe Val Asn Ala Gln Met Ala Ala Lys<br>               620                       625                       630 | 1925 |
| gaa atg tgc aag gaa atg aat gtc gag gct att ttg aaa caa aaa aga<br>Glu Met Cys Lys Glu Met Asn Val Glu Ala Ile Leu Lys Gln Lys Arg<br>635                           640                       645 | 1973 |
| ata aga tcc aca aag tgc caa ttc tcg tat gaa tca cac gat gag cct<br>Ile Arg Ser Thr Lys Cys Gln Phe Ser Tyr Glu Ser His Asp Glu Pro<br>650                           655                       660 | 2021 |
| ttc agt gac gca ctt aaa aag ttg gag gtt gaa ttt tca aat gtt gtt<br>Phe Ser Asp Ala Leu Lys Lys Leu Glu Val Glu Phe Phe Asn Val Val<br>665                           670                       675             680 | 2069 |
| gtt gat gaa gcc ttg tca gcc atc gcg gag agg ttt tcc aca ttg gaa<br>Val Asp Glu Ala Leu Ser Ala Ile Ala Glu Arg Phe Ser Thr Leu Glu<br>               685                       690                       695 | 2117 |
| gtt gta caa aac aga ttt ggg gtt ttg acc aat ttc cca agc ctt gga<br>Val Val Gln Asn Arg Phe Gly Val Leu Thr Asn Phe Pro Ser Leu Gly<br>            700                     705                       710 | 2165 |
| gac gag gag ctg acg gag caa tgc gag gca cta ggc aac ata ctc cat<br>Asp Glu Glu Leu Thr Glu Gln Cys Glu Ala Leu Gly Asn Ile Leu His<br>               715                       720                       725 | 2213 |
| ttt gag aag aac tgg gat ttg gac agt aga gag ctt gtt cag gaa atc<br>Phe Glu Lys Asn Trp Asp Leu Asp Ser Arg Glu Leu Val Gln Glu Ile<br>730                           735                       740 | 2261 |

```
aag aac ttg cct aac tta cca tca acg act cca agt ctc ctt gag ctc       2309
Lys Asn Leu Pro Asn Leu Pro Ser Thr Thr Pro Ser Leu Leu Glu Leu
745                 750                 755                 760 atc tct ttc atg tct gat aag gat cta tca gaa atc tat ccg aac ttt       2357
Ile Ser Phe Met Ser Asp Lys Asp Leu Ser Glu Ile Tyr Pro Asn Phe
                765                 770                 775 tgg act gct ctc agg att gca ctc acc ttg cca gtc act gtg gct caa       2405
Trp Thr Ala Leu Arg Ile Ala Leu Thr Leu Pro Val Thr Val Ala Gln
            780                 785                 790 gca gag agg agc ttt tca aaa cta aaa ttg atc aag tcg tac ctg agg       2453
Ala Glu Arg Ser Phe Ser Lys Leu Lys Leu Ile Lys Ser Tyr Leu Arg
        795                 800                 805 tca aca atg tca cag gag cga ctc act aac ctt gcc gtt gtt agc atc       2501
Ser Thr Met Ser Gln Glu Arg Leu Thr Asn Leu Ala Val Val Ser Ile
    810                 815                 820 aat cac tca gta ggg gag cag ata tca tat gat gat gtt att gac gag       2549
Asn His Ser Val Gly Glu Gln Ile Ser Tyr Asp Asp Val Ile Asp Glu
825                 830                 835                 840 ttt gca tca aga aag gct agg aag gtt agg ttt tag ttggtgtttt            2595
Phe Ala Ser Arg Lys Ala Arg Lys Val Arg Phe
                845                 850 ctgttattgt attggtgctg cagttatatt tattttagcg tgtcatttgt gtgataaaag     2655
gtttgtgctt tataatattt attttatatt atttattcaa tattgagttt gattcaatat     2715
tttcttagct aactgtattt ttgccatgct                                      2745

<210> SEQ ID NO 17
<211> LENGTH: 851
<212> TYPE: PRT
<213> ORGANISM: Oryzias latipes

<400> SEQUENCE: 17

Met Glu Lys Lys Arg Ser Lys Pro Ser Gly Ala Gln Phe Arg Lys Lys
1               5                   10                  15

Arg Lys Glu Glu Glu Lys Arg Asp Lys Glu Lys Gly Ala Leu Leu
            20                  25                  30

Arg Tyr Phe Gly Ser Ser Thr Thr Ala Gln Asp Glu Thr Ser Thr Ser
        35                  40                  45

Leu Pro Ala Ile Ser Ser Ala Thr Val Thr Val Ser Pro Pro Gln Asp
    50                  55                  60

Glu Leu Pro Ser Thr Ser Ser Ala Thr His Val Val Pro Gln Leu Leu
65                  70                  75                  80

Pro Glu Gln Ser Phe Asp Ser Glu Ala Glu Asp Val Val Pro Ser Thr
                85                  90                  95

Ser Thr Gln Leu Glu Thr Ser Glu Met Pro Gly Asp Glu Thr Pro Leu
            100                 105                 110

Thr Pro Thr Ala Glu Asp Gln Pro Leu Pro Thr Asp Pro Ala Lys Trp
        115                 120                 125

Pro Ser Pro Leu Thr Asp Arg Ile Arg Met Glu Leu Val Arg Arg Gly
    130                 135                 140

Pro Ser Ser Ile Pro Pro Asp Phe Val Phe Pro Arg Asn Asp Ser Asp
145                 150                 155                 160

Gly Arg Ser Cys His His Tyr Phe Arg Lys Thr Leu Val Ser Gly
                165                 170                 175

Glu Lys Ile Ala Arg Thr Trp Leu Met Tyr Ser Lys Val Lys Asn Ser
            180                 185                 190
```

-continued

```
Leu Phe Cys Phe Cys Cys Lys Leu Phe Ser Asn Lys Asn Ile Asn Leu
            195                 200                 205
Thr Thr Ser Gly Thr Ala Asn Trp Lys His Ala Ser Thr Tyr Leu Thr
210                 215                 220
Ala His Glu Lys Ser Pro Glu His Leu Asn Cys Met Lys Ala Trp Lys
225                 230                 235                 240
Glu Leu Ser Gly Arg Ile Arg Ser Gly Lys Thr Ile Asp Lys Gln Glu
            245                 250                 255
Met Ala Leu Leu Glu Glu Arg Val Arg Trp Arg Ala Val Leu Thr
                260                 265                 270
Arg Leu Ile Ala Ile Val Gln Ser Leu Ala Val Arg Asn Leu Ala Leu
            275                 280                 285
Arg Gly His Thr Glu Thr Leu Phe Thr Ser Ser Asn Gly Asn Phe Leu
290                 295                 300
Lys Glu Val Glu Leu Met Ala Arg Phe Asp Pro Ile Met Lys Asp His
305                 310                 315                 320
Leu Asn Arg Val Leu Arg Gly Thr Ala Ser His Asn Ser Tyr Ile Gly
            325                 330                 335
His His Val Gln Asn Glu Leu Ile Asp Leu Leu Ser Ser Lys Ile Leu
            340                 345                 350
Ser Ala Ile Val Asp Asp Ile Lys Lys Ala Lys Tyr Phe Ser Ile Ile
            355                 360                 365
Leu Asp Cys Thr Leu Asp Ile Ser His Thr Glu Gln Leu Ser Val Ile
            370                 375                 380
Ile Arg Val Val Ser Leu Met Glu Lys Pro Gln Ile Arg Glu His Phe
385                 390                 395                 400
Met Gly Phe Leu Glu Ala Glu Ser Thr Gly Gln His Leu Ala Ser
            405                 410                 415
Met Ile Leu Asn Arg Leu Glu Glu Leu Gly Ile Ser Phe Glu Asp Cys
            420                 425                 430
Arg Gly Gln Ser Tyr Asp Asn Gly Ala Asn Met Lys Gly Lys Asn Lys
            435                 440                 445
Gly Val Gln Ala Arg Leu Leu Glu Lys Asn Pro Arg Ala Leu Phe Leu
450                 455                 460
Pro Cys Gly Ala His Thr Leu Asn Leu Val Val Cys Asp Ala Ala Lys
465                 470                 475                 480
Arg Ser Val Asp Ala Met Ser Tyr Phe Gly Val Leu Gln Lys Leu Tyr
            485                 490                 495
Thr Leu Phe Ser Ala Ser Ala Gln Arg Trp Ala Ile Leu Lys Ser Gln
            500                 505                 510
Val Ser Ile Thr Leu Lys Ser Trp Thr Glu Thr Arg Trp Glu Ser Lys
            515                 520                 525
Ile Lys Ser Ile Glu Pro Met Arg Tyr Gln Gly Ala Ala Val Arg Glu
530                 535                 540
Ala Leu Ile Glu Val Arg Asp Lys Thr Lys Asp Pro Val Ile Lys Ala
545                 550                 555                 560
Glu Ala Gln Ser Leu Ser Glu Glu Val Gly Ser Tyr Arg Phe Asn Ile
            565                 570                 575
Cys Thr Val Val Trp His Asp Ile Leu Ser Thr Ile Lys His Val Ser
                580                 585                 590
Lys Leu Met Gln Ser Pro Asn Met His Val Asp Leu Ala Val Ser Leu
            595                 600                 605
Leu Lys Lys Thr Glu Gln Ser Leu Gln Ser Tyr Arg Ala Asn Gly Phe
```

```
                610                615                620
Val Asn Ala Gln Met Ala Ala Lys Glu Met Cys Lys Glu Met Asn Val
625                630                635                640

Glu Ala Ile Leu Lys Gln Lys Arg Ile Arg Ser Thr Lys Cys Gln Phe
            645                650                655

Ser Tyr Glu Ser His Asp Glu Pro Phe Ser Asp Ala Leu Lys Lys Leu
            660                665                670

Glu Val Glu Phe Phe Asn Val Val Asp Glu Ala Leu Ser Ala Ile
        675                680                685

Ala Glu Arg Phe Ser Thr Leu Glu Val Val Gln Asn Arg Phe Gly Val
    690                695                700

Leu Thr Asn Phe Pro Ser Leu Gly Asp Glu Glu Leu Thr Glu Gln Cys
705                710                715                720

Glu Ala Leu Gly Asn Ile Leu His Phe Glu Lys Asn Trp Asp Leu Asp
            725                730                735

Ser Arg Glu Leu Val Gln Glu Ile Lys Asn Leu Pro Asn Leu Pro Ser
            740                745                750

Thr Thr Pro Ser Leu Leu Glu Leu Ile Ser Phe Met Ser Asp Lys Asp
        755                760                765

Leu Ser Glu Ile Tyr Pro Asn Phe Trp Thr Ala Leu Arg Ile Ala Leu
    770                775                780

Thr Leu Pro Val Thr Val Ala Gln Ala Glu Arg Ser Phe Ser Lys Leu
785                790                795                800

Lys Leu Ile Lys Ser Tyr Leu Arg Ser Thr Met Ser Gln Glu Arg Leu
            805                810                815

Thr Asn Leu Ala Val Val Ser Ile Asn His Ser Val Gly Glu Gln Ile
            820                825                830

Ser Tyr Asp Asp Val Ile Asp Glu Phe Ala Ser Arg Lys Ala Arg Lys
        835                840                845

Val Arg Phe
    850
```

PROTEIN PRODUCTION METHOD

This is a continuation of U.S. patent application Ser. No. 12/813,920 (allowed), filed Jun. 11, 2010, which claims the benefit of U.S. Provisional Patent Application No. 61/186,138, filed Jun. 11, 2009, and which claims priority to Japanese Patent Application No. 2009-140626, filed Jun. 11, 2009, the contents of all of which are incorporated herein by reference in their entirety.

BACKGROUND OF THE INVENTION

1. Field of the Invention

This invention relates to a method for producing a protein of interest, comprising introducing a protein expression vector which comprises a gene fragment comprising a DNA encoding a protein of interest and a selectable marker gene and transposon sequences at both terminals of the gene fragment, into a suspension mammalian cell, integrating the gene fragment inserted between a pair of the transposon sequences into a chromosome of the mammalian cell to obtain a mammalian cell capable of expressing the protein of interest; and suspension-culturing the mammalian cell; and a suspension mammalian cell capable of expressing the protein of interest.

2. Brief Description of the Background Art

Production of exogeneous proteins by recombinant DNA techniques is used in various industries such as pharmaceutical industry and food industry. In most cases, production of recombinant proteins is carried out by introducing an expression vector comprising a nucleotide sequence encoding a protein of interest into a host, such as *Escherichia coli*, yeast, insect cell, plant cell, and animal cell, selecting a transformant in which the expression vector is integrated into the chromosome, and further culturing the cell line under appropriate culture conditions.

However, in order to develop a host which can produce an exogeneous protein efficiently, it is necessary to select a host cell having good productivity for each protein of interest, so that a further technical innovation is desired on the exogeneous protein production techniques for individual host.

In the bacteria systems, such as *Escherichia coli*, and yeast systems, different from animal cells, post-translational modifications, such as sugar chain modification, are difficult to attain in many cases and thus cause a problem in producing a protein having its activity.

Since the produced protein is subject to a post-translational modification such as phosphrylation and addition of sugar chains in the insect system, this system has a merit that the protein having its original physiological activity can be expressed. However, since the sugar chain structure of the secreted protein is different from that of mammalians-derived cells, antigenicity and the like become a problem when the protein is applied to pharmaceutical use.

In addition, since a recombinant virus is used in the insect cell system when an exogeneous gene is introduced, there is a problem that its inactivation and containment of the virus are required from the viewpoint of safety.

In the animal cell system, post-translational modifications, such as phosphorylation, sugar chain addition, and folding, can be conducted to proteins derived from higher animals including human, in more similar manner to those produced in the living body. Such accurate post-translational modifications are necessary for recreating the physiological activity originally possessed by a protein in its recombinant protein, and a protein production system in which a mammalian cell is used as a host is usually applied to pharmaceutical products and the like that requires such physiological activity.

However, a protein expression system in which a mammalian cell is used as the host is generally low in productivity, and also causes a problem of the stability of introduced genes in many cases. Improvement of productivity of a protein using a mammalian culture cell as a host is not only very important in producing medicaments for treatment, diagnostic agents and the like, but also greatly contributes to research and development of them. Thus, it is urgent to develop a gene expression system which easily makes it possible to obtain a cell line of a high productivity using a mammalian culture cell, particularly Chinese hamster ovary cell (CHO cell), as the host.

A transposon is a transposable genetic element which can transfer from one locus to other locus on the chromosome. A transposon is a strong tool for the study on molecular biology and genetics and used for a purpose, such as mutagenesis, gene trapping, and preparation of transgenic individuals, in insects or nematode (e.g., *Drosophila melanogaster* or *Caenorhabditis elegans*) and plants. However, development of such a technique has been delayed for vertebral animals including mammalian cells.

In recent years, however, transposons which have activities also in vertebral animals have been reported, and some of them were shown to have an activity in mammalian cells, such as cell derived from mouse and human. Typical examples include transposons Tol1 (Patent Reference 1) and Tol2 (Non-patent Reference 1) cloned from a medaka (killifish), Sleeping Beauty reconstructed from a non-autonomous transposon existed in *Onchorhynchus* fish genome (Non-patent Reference 2), an artificial transposon Frog prince (Non-patent Reference 3) which is derived from frog and a transposon piggyBac (Non-patent Reference 4) which is derived from insect.

These DNA transposons have been used for mutagenesis, gene trapping, preparation of transgenic individuals, expression of drug-resistant proteins, and the like, as a gene transfer tool for bringing a new phenotype in a genome of a mammalian cell (Non-patent References 5 to 12).

In the case of insects, a method in which an exogeneous gene is introduced into silkworm chromosome using the transposon piggyBac derived from a Lepidoptera insect to express the protein encoded by said exogeneous gene was studied, and a protein production method using the above techniques has been disclosed (Patent Reference 2).

However, since the expressed protein of interest is not sufficient in expression level and is produced in the whole body of silkworm, it causes an economical problem due to the necessity of an advanced purification technique for recovering the expressed exogeneous protein in a highly purified form from the body fluid including a large amount of contaminated proteins.

In addition, an example in which a protein relating to G418 resistance is expressed in a mammalian cell using the medaka-derived transposon Tol2 (Non-patent Reference 12) is known.

CITATION LIST

Patent Literature

[Patent Literature 1] WO2008/072540
[Patent Literature 2] Japanese Published Unexamined Patent Application No. 2001-532188

Non Patent Literature

[Non Patent Literature 1] *Nature* 383, 30 (1996)
[Non Patent Literature 2] *Cell* 91, 501-510 (1997)

[Non Patent Literature 3] *Nucleic Acids Res,* 31, 6873-6881 (2003)
[Non Patent Literature 4] *Insect Mol. Biol.* 5, 141-151 (1996)
[Non Patent Literature 5] *Genetics.* 166, 895-899 (2004)
[Non Patent Literature 6] *PLoS Genet,* 2, e169 (2006)
[Non Patent Literature 7] *Proc. Natl. Acad. Sci. USA* 95, 10769-10773 (1998)
[Non Patent Literature 8] *Proc. Natl. Acad. Sci. USA* 98:6759-6764 (2001)
[Non Patent Literature 9] *Nature* 436, 221-22 6 (2005)
[Non Patent Literature 10] *Nucleic Acids Res.,* 31, 6873-6881 (2003)
[Non Patent Literature 11] *Nucleic Acids Res.,* 35, e87 (2007)
[Non Patent Literature 12] *Proc Natl. Acad. Sci. USA,* 103, 15008-15013 (2006)

SUMMARY OF THE INVENTION

In order to produce and analyze a protein of interest, it is necessary to select a cell line which stably and highly expresses a protein of interest, using a mammalian-derived culture cell, but preparation and culture of the cell that produces the protein of interest require considerable labor and time.

In addition, though it is known that a protein of interest is expressed in a mammalian cell using a transposon sequence, preparation of a cell which can highly express a protein of interest and thus can be used as a protein production system by using a transposon sequence; preparation method of a mammalian cell which can highly produce a protein of interest by using a transposon sequence; and a production method of a protein using the cell are not known.

As described in the above, the expression of a protein of interest in a large amount by establishing a protein production system which can highly produce a protein of interest using a mammalian culture cell efficiently and within a short period has been required. Thus, the objects of the invention are to provide a cell capable of highly expressing a protein of interest which can be efficiently established, and a method for producing the protein of interest using the cell.

Solution to Problems

To solve the above-mentioned problems, the present inventors have conducted intensive studies and found as a result that a mammalian cell capable of highly expressing a protein of interest can be efficiently prepared by introducing a protein expression vector which comprises a gene fragment comprising a DNA encoding the protein of interest and a selectable marker gene and transposon sequences at both terminals of the gene fragment, into a suspension mammalian cell; and integrating the gene fragment inserted between a pair (two) of the transposon sequences into a chromosome of the mammalian cell. In addition, it was found that the protein of interest can be produced efficiently by using the cell, and thereby the invention was accomplished.

According to the protein production method of the invention, a protein of interest can be efficiently produced by the use of a mammalian cell. In addition, the cell of the invention can be used as a protein production cell for producing a recombinant protein with a high efficiency.

Tol2-L represents a left end Tol2 transposon (SEQ ID NO:2), Tol2-R represents a right end Tol2 transposon (SEQ ID NO:3), CMV represents a CMV promoter, poly A represents a polyadenylation site, Hc represents a human antibody H chain cDNA, Lc represents a human antibody L chain cDNA, and CHX-r represents a cycloheximide resistance gene.

Figure 2:
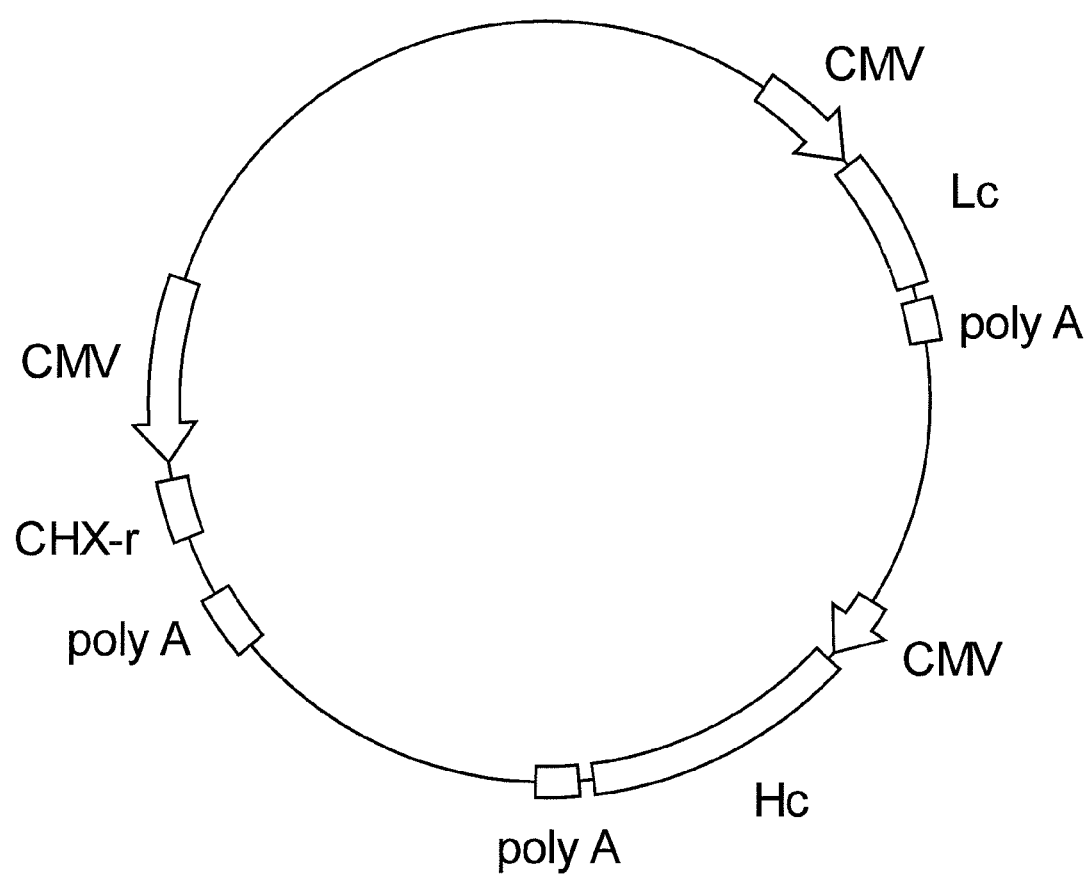

FIG. 2 shows a schematic illustration of an anti-human influenza M2 antibody expression vector. CMV represents a CMV promoter, poly A represents a polyadenylation site, Hc represents a human antibody H chain cDNA, Lc represents a human antibody L chain cDNA and CHX-r represents a cycloheximide resistance gene.

Figure 3:
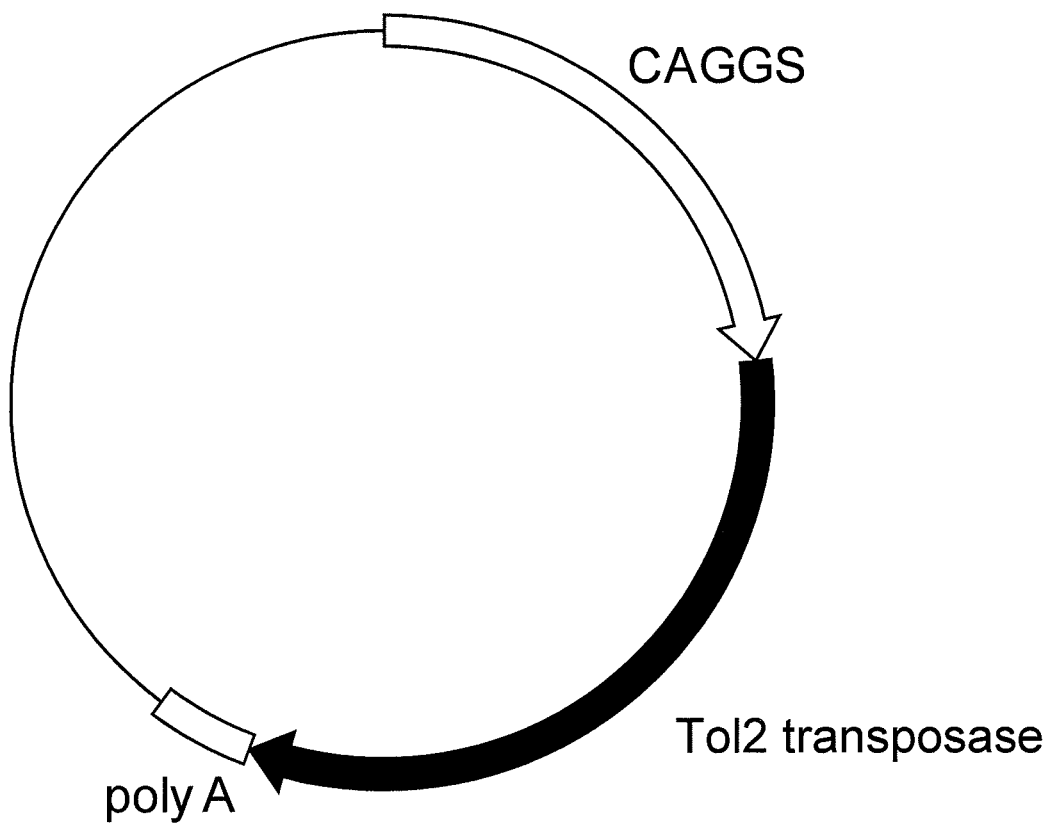

FIG. 3 shows a schematic illustration of a Tol2 transposase expression vector. CAGGS represents a CAGGS promoter, poly A represents a polyadenylation site, and TPase cDNA represents a Tol2 transposase cDNA.

Figure 4A:
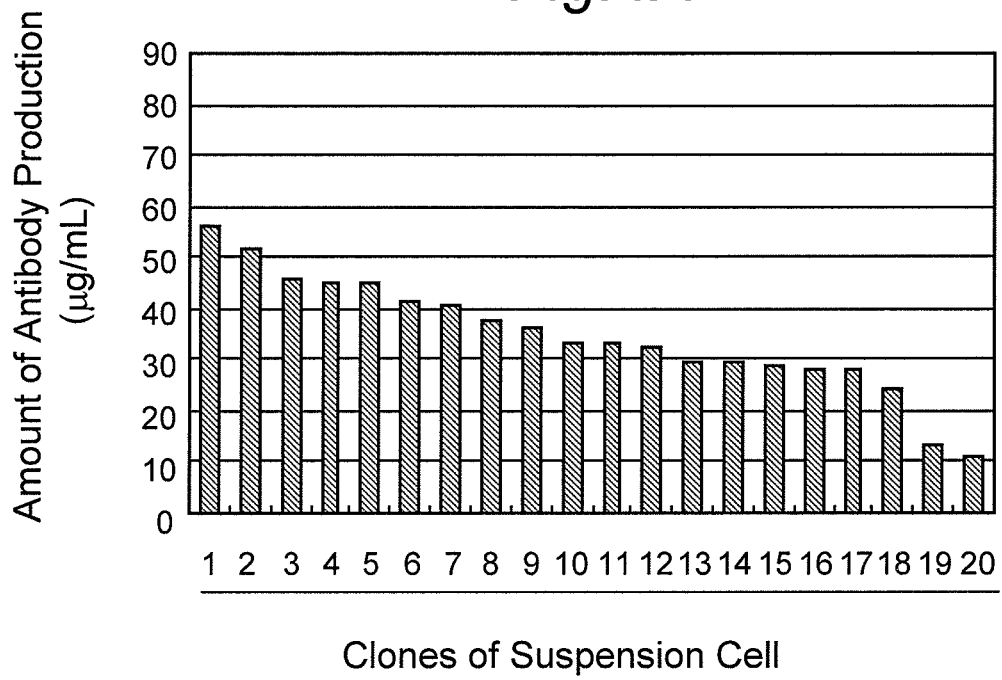

FIG. 4A shows a result of examining expression level of an anti-human influenza M2 antibody in a suspension CHO-K1 cell when a Tol2 transposon vector for expressing an anti-human influenza M2 antibody was used. The ordinate shows the amount of antibody production (μg/ml), and the abscissa shows the number of transgenic clones of the suspension CHO-K1 cell.

Figure 4B:
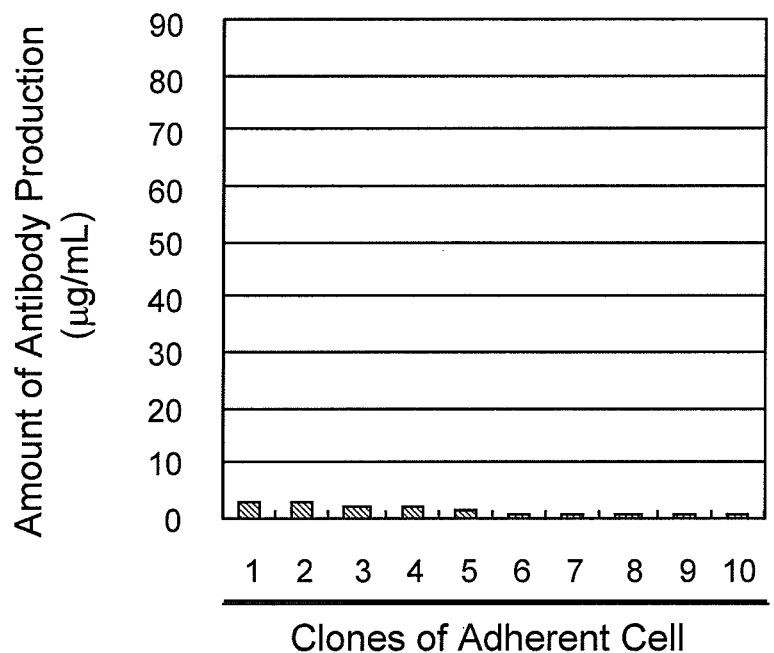

FIG. 4B shows a result of examining expression level of an anti-human influenza M2 antibody in an adhesive CHO-K1 cell when a Tol2 transposon vector for expressing an anti-human influenza M2 antibody was used. The ordinate shows the amount of antibody production (μg/ml), and the abscissa shows the number of transgenic clones of the adhesive CHO-K1 cell.

Figure 5:
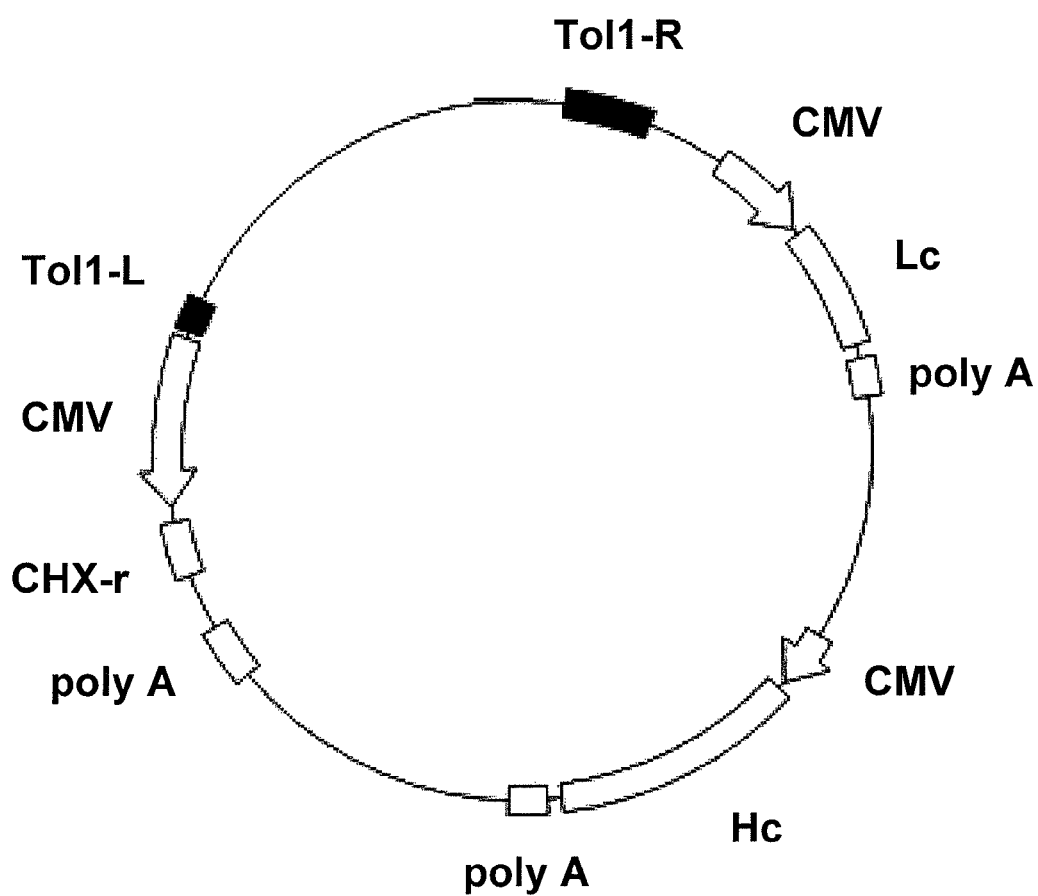

FIG. 5 shows a schematic illustration of a Tol1 transposon vector for expressing an anti-human influenza M2 antibody. Tol1-L represents a left end Tol1 transposon (SEQ ID NO:14), Tol1-R represents a right end Tol1 transposon (SEQ ID NO:15), CMV represents a CMV promoter, poly A represents a polyadenylation site, Hc represents a human antibody H chain cDNA, Lc represents a human antibody L chain cDNA, and CHX-r represents a cycloheximide resistance gene.

Figure 6:
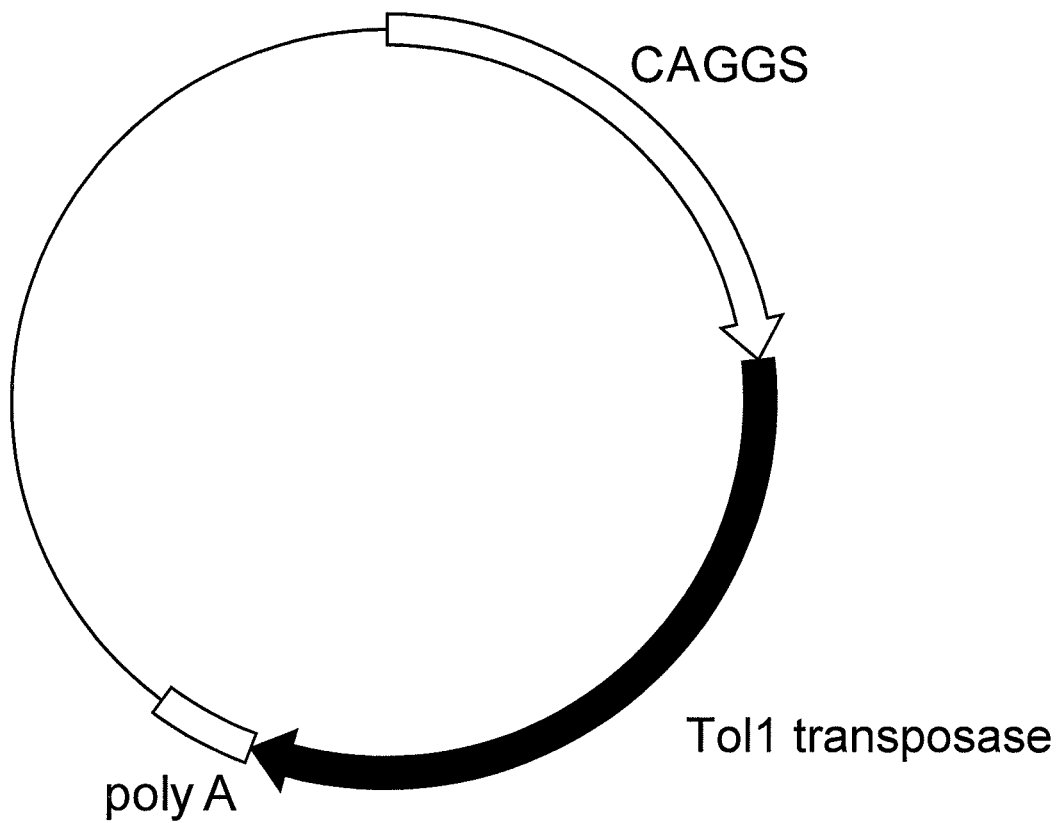

FIG. 6 shows a schematic illustration of a Tol1 transposase expression vector. CAGGS represents a CAGGS promoter, poly A represents a polyadenylation site, and TPase cDNA represents a Tol1 transposase cDNA.

Figure 7:
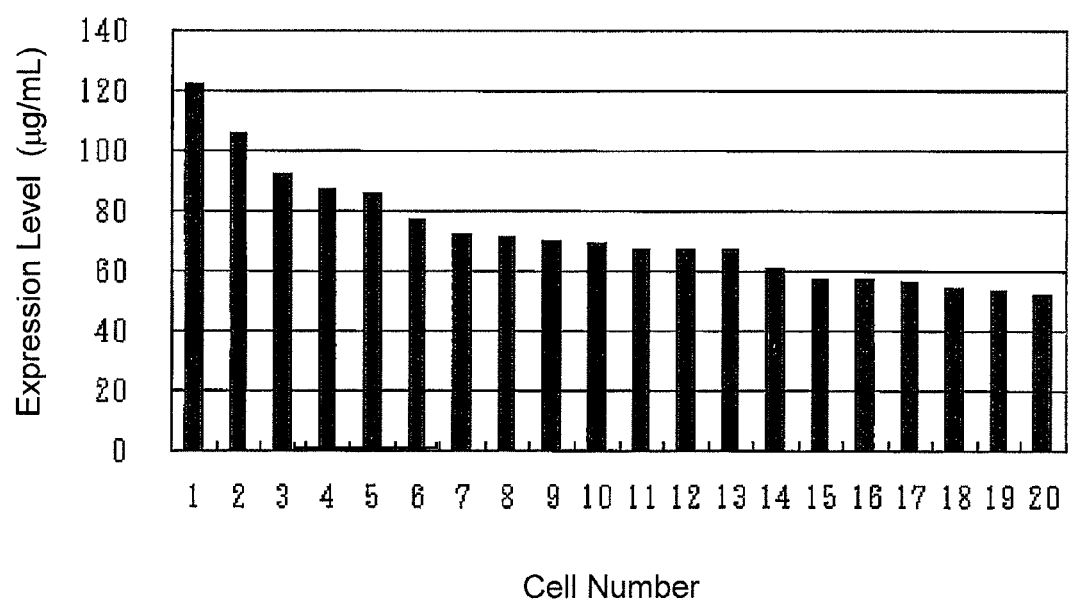

FIG. 7 shows a result of examining expression level of an anti-human influenza M2 antibody in a suspension CHO-K1 cell when a Tol1 transposon vector for expressing an anti-human influenza M2 antibody was used. The ordinate shows the amount of antibody production (μg/ml), and the abscissa shows the number of transgenic clones of the suspension CHO-K1 cell.

DETAILED DESCRIPTION OF THE INVENTION

Specifically, the invention relates to the following 1 to 31:
1. A method for producing a protein of interest, comprising introducing a protein expression vector which comprises a gene fragment comprising a DNA encoding a protein of interest and a selectable marker gene and transposon sequences at both terminals of the gene fragment, into a suspension mammalian cell; integrating the gene fragment inserted between a pair of the transposon sequences into a chromosome of the mammalian cell to obtain a mammalian cell capable of expressing the protein of interest; and suspension-culturing the mammalian cell; 2. A method for producing a protein of interest, comprising the following steps (A) to (C):

(A) a step of simultaneously introducing the following expression vectors (a) and (b) into a suspension mammalian cell:
  (a) an expression vector which comprises a gene fragment comprising a DNA encoding a protein of interest and transposon sequences at both terminals of the gene fragment,
  (b) an expression vector which comprises a DNA encoding a transposase which recognizes the transposon sequences and has activity of transferring a gene fragment inserted between a pair of the transposon sequences into a chromosome,
(B) a step of expressing transiently the transposase from the expression vector introduced in the step (A) to integrate the gene fragment inserted between a pair of the transposon sequences into a chromosome of the mammalian cell to obtain a suspension mammalian cell capable of expressing the protein of interest, and
(C) a step of suspension-culturing the suspension mammalian cell capable of expressing the protein of interest obtained in the step (B) to produce the protein of interest;

3. A method for obtaining a suspension mammalian cell capable of expressing a protein of interest, comprising introducing a protein expression vector which comprises a gene fragment comprising a DNA encoding a protein of interest and a selectable marker gene and transposon sequences at both terminals of the gene fragment into a suspension mammalian cell; and integrating the gene fragment inserted between a pair of the transposon sequences, into a chromosome of the mammalian cell;

4. The method described in any one of the aforementioned items 1 to 3, wherein the suspension mammalian cell is a cell capable of surviving and proliferating in a serum-free medium;

5. The method described in any one of the aforementioned items 1 to 4, wherein the suspension mammalian cell is at least one selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

6. The method described in the aforementioned item 5, wherein the CHO cell is at least one selected from CHO-K1, CHO-K1SV, DUKXB11, CHO/DG44, Pro-3 and CHO-S;

7. The method described in any one of the aforementioned items 1 to 6, wherein the selectable marker gene is a cycloheximide resistance gene;

8. The method described in the aforementioned item 7, wherein the cycloheximide resistance gene is a gene encoding a mutant of human ribosomal protein L36a;

9. The method described in the aforementioned item 8, wherein the mutant is a mutant in which proline at position 54 of the human ribosomal protein L36a is substituted with other amino acid;

10. The method described in the aforementioned item 9, wherein the other amino acid is glutamine;

11. The method described in any one of the aforementioned items 1 to 10, wherein a pair of the transposon sequences are nucleotide sequences derived from a pair of DNA-type transposons which function in a mammalian cell;

12. The method described in the aforementioned item 11, wherein the nucleotide sequences derived from a pair of DNA type transposons are nucleotide sequences derived from a pair of Tol1 transposons or nucleotide sequences derived from a pair of Tol2 transposons;

13. The method described in the aforementioned item 12, wherein the nucleotide sequences derived from a pair of Tol2 transposons are a nucleotide sequence comprising the nucleotide sequence shown in SEQ ID NO:2 and the nucleotide sequence shown in SEQ ID NO:3;

14. The method described in the aforementioned item 12, wherein the nucleotide sequences derived from a pair of Tol1 transposons are the nucleotide sequence shown in SEQ ID NO:14 and the nucleotide sequence shown in SEQ ID NO:15;

15. A suspension mammalian cell capable of producing a protein of interest, into which a protein expression vector comprising a gene fragment comprising a DNA encoding a protein of interest and a selectable marker gene and transposon sequences at both terminals of the gene fragment is introduced, to integrate the gene fragment inserted between a pair of the transposon sequences into a chromosome;

16. A suspension mammalian cell capable of producing a protein of interest, into which an expression vector (a) comprising a gene fragment comprising a DNA encoding a protein of interest and a selectable marker gene and transposon sequences at both terminals of the gene fragment, and an expression vector (b) comprising a DNA encoding a transposase (a transferase) which recognizes the transposon sequences and has activity of transferring the gene fragment inserted between a pair of the transposon sequences into a chromosome to integrate the gene fragment inserted between a pair of the transposon sequences into the chromosome;

17. The cell described in the aforementioned item 15 or 16, wherein the cell is a cell capable of surviving and proliferating in a serum-free medium;

18. The cell described in any one of the aforementioned items 15 to 17, wherein the cell is at least one suspension mammalian cell selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

19. The cell described in the aforementioned item 18, wherein the CHO cell is at least one selected from CHO-K1, CHO-K1SV, DUKXB11, CHO/DG44, Pro-3 and CHO-S;

20. The cell described in any one of the aforementioned items 15 to 19, wherein the selectable marker gene is a cycloheximide resistance gene;

21. The cell described in the aforementioned item 20, wherein the cycloheximide resistance gene is a gene encoding a mutant of human ribosomal protein L36a;

22. The cell described in the aforementioned item 21, wherein the mutant is a mutant in which proline at position 54 of the human ribosomal protein L36a is substituted with other amino acid;

23. The cell described in the aforementioned item 22, wherein the other amino acid is glutamine;

24. The cell described in any one of the aforementioned items 15 to 23, wherein a pair of the transposon sequences are nucleotide sequences derived from a pair of DNA-type transposons which function in a mammalian cell;

25. The cell described in the aforementioned item 24, wherein the nucleotide sequences derived from a pair of the DNA-type transposons are nucleotide sequences derived from a pair of Tol1 transposons or nucleotide sequences derived from a pair of Tol2 transposons;

26. The cell described in the aforementioned item 25, wherein the nucleotide sequences derived from a pair of the Tol2 transposons are the nucleotide sequence shown in SEQ ID NO:2 and the nucleotide sequence shown in SEQ ID NO:3;

27. The cell described in the aforementioned item 25, wherein the nucleotide sequences derived from a pair of the Tol1 transposons are the nucleotide sequence shown in SEQ ID NO:14 and the nucleotide sequence shown in SEQ ID NO:15;

28. A protein expression vector, comprising a gene fragment comprising a DNA encoding a protein of interest and a selectable marker gene, and a pair of transposon sequences at both terminals of the gene fragment;

29. The protein expression vector described in the aforementioned item 28, wherein a pair of the transposon sequences are nucleotide sequences derived from a pair of Tol1 transposons or nucleotide sequences derived from a pair of Tol2 transposons.

30. The protein expression vector described in the aforementioned item 29, wherein the nucleotide sequences derived from a pair of the Tol2 transposons are the nucleotide sequence shown in SEQ ID NO:2 and the nucleotide sequence shown in SEQ ID NO:3; and 31. The protein expression vector described in the aforementioned item 29, wherein the nucleotide sequences derived from a pair of the Tol1 transposons are the nucleotide sequence shown in SEQ ID NO:14 and the nucleotide sequence shown in SEQ ID NO:15.

This invention relates to a method for producing a protein of interest, comprising introducing a protein expression vector comprising a gene fragment comprising a DNA encoding a protein of interest and a selectable marker gene and transposon sequences at both terminals of the gene fragment, into a suspension mammalian cell; integrating the gene fragment inserted between a pair (two) of the transposon sequences, into a chromosome of the mammalian cell to obtain a mammalian cell capable of expressing said protein of interest; and suspension-culturing the mammalian cell.

Examples of the method for producing a protein of interest of the present invention include a method, comprising the following steps (A) to (C):
(A) a step of simultaneously introducing the following expression vectors (a) and (b) into a suspension mammalian cell:
(a) an expression vector which comprises a gene fragment comprising a DNA encoding a protein of interest and transposon sequences at both terminals of the gene fragment,
(b) an expression vector which comprises a DNA encoding a transposase which recognizes the transposon sequences and has activity of transferring a gene fragment inserted between a pair of the transposon sequences into a chromosome,
(B) a step of expressing transiently the transposase transiently from the expression vector introduced in the step (A) to integrate the gene fragment inserted between a pair of the transposon sequences into a chromosome of the mammalian cell to obtain a suspension mammalian cell capable of expressing the protein of interest, and
(C) a step of suspension-culturing the suspension mammalian cell capable of expressing the protein of interest obtained in the step (B) to produce the protein of interest.

In addition, the present invention relates to a suspension mammalian cell capable of producing a protein of interest, into which a protein expression vector comprising a gene fragment comprising a DNA encoding a protein of interest and a selectable marker gene and transposon sequences at both terminals of the gene fragment is introduced, to integrate the gene fragment inserted between a pair of the transposon sequences into a chromosome.

Furthermore, the present invention relates to a suspension mammalian cell capable of producing a protein of interest, into which an expression vector (a) comprising a gene fragment comprising a DNA encoding a protein of interest and a selectable marker gene and transposon sequences at both terminals of the gene fragment, and an expression vector (b) comprising a DNA encoding a transposase (a transferase) which recognizes the transposon sequences and has activity of transferring the gene fragment inserted between a pair of the transposon sequences into a chromosome to integrate the gene fragment inserted between a pair of the transposon sequences into the chromosome.

The term "transposon" in the present specification is a transposable genetic element and means a gene unit which moves on a chromosome or from a chromosome to other chromosome (transposition) while keeping a certain structure.

The transposon comprises a gene unit of a repeating transposon sequences (also called inverted repeat sequence (IR sequence) or terminal inverted repeat sequence (TIR sequence)) which positions in the same direction or the reverse direction at both terminals of the gene unit and a nucleotide sequence encoding a transposase which recognizes the transposon sequence to transfer a gene existing between the transposon sequences.

The transposase translated from the transposon can transfer a DNA by recognizing transposon sequences of both terminals of the transposon, cutting out the DNA fragment inserted between a pair of the transposon sequences and inserting the fragment into the site to be transferred.

The term "transposon sequence" in the present specification means the nucleotide sequence of a transposon recognized by a transposase and has the same meaning as the IR sequence or TIR sequence. A DNA comprising the nucleotide sequence may comprise an imperfect repeating moiety as long as it can be transferred (inserted into other position in the genome) by the activity of a transposase, and comprise a transposon sequence specific to the transposase.

As the transposon sequence to be used in the invention, a nucleotide sequence derived from a DNA-type transposon is preferable, and a nucleotide sequence derived from a pair of natural or artificial DNA-type transposons, which can be recognized by a transposase and be transposed in mammalian cells, is more preferable.

Examples of the nucleotide sequence derived from a DNA-type transposon include the nucleotide sequences derived from the medaka fish-derived Tol1 transposon and Tol2 transposon, the Sleeping Beauty reconstructed from a non-autonomous transposon existed in an *Onchorhynchus* fish genome, the frog-derived artificial transposon Frog prince and the insect-derived transposon PiggyBac.

Particularly, among them, the nucleotide sequences derived from the medaka fish-derived Tol2 transposon comprising the nucleotide sequence shown in SEQ ID NO:6 and the medaka fish-derived Tol2 transposon comprising the nucleotide sequence shown in SEQ ID NO:13 are preferable.

Examples of the nucleotide sequence derived from a pair of Tol2 transposons include the nucleotide sequence at positions 1 to 2229 and the nucleotide sequence at positions 4148 to 4682 in the Tol2 transposon nucleotide sequence shown in SEQ ID NO:6 of Sequence Listing.

As the nucleotide sequence derived from a pair of Tol2 transposons, the nucleotide sequence at positions 1 to 200 (SEQ ID NO:2) (hereinafter referred to as "Tol2-L sequence") and the nucleotide sequence at positions 2285 to 2788 (SEQ ID NO:3) (hereinafter referred to as "Tol2-R sequence") in the Tol2 transposon nucleotide sequence shown in SEQ ID NO:1 of Sequence Listing are more preferable.

Examples of the nucleotide sequence derived from a pair of Tol1 transposons include the nucleotide sequence comprising a nucleotide sequence at positions 1 to 157 and the nucleotide sequence at positions the 1748 to 1855 in the Tol1 transposon nucleotide sequence shown in SEQ ID NO:13 of Sequence Listing.

As the nucleotide sequence derived from a pair of Tol1 transposons, the nucleotide sequence at positions 1 to 200 (SEQ ID NO:14) (hereinafter referred to as "Tol1-L sequence") and the nucleotide sequence at positions 1351 to 1855 (SEQ ID NO:15) (hereinafter referred to as "Tol1-R sequence") in the Tol2 transposon nucleotide sequence shown in SEQ ID NO:1 of Sequence Listing are more preferable.

Examples of the transposon sequence to be used in the invention include transposon sequences of which transfer reactions are controlled by using a partial sequence of a transposon sequence derived from the above-mentioned transposon, by adjusting the length of the nucleotide sequence and by modifying the nucleotide sequence due to addition, deletion or substitution.

Regarding the control of the transfer reaction of a transposon, the transfer reaction can be accelerated or suppressed by accelerating or suppressing recognition of the transposon sequence by a transposase, respectively.

The term "transposase" in the present specification means an enzyme which recognizes nucleotide sequences having transposon sequences and transfers a DNA existing between the nucleotide sequences into a chromosome or from the chromosome to other chromosome.

Examples of the transposase include the Tol1 and Tol2 which are derived from medaka fish, the Sleeping Beauty reconstructed from a non-autonomous transposon existed in an *Onchorhynchus* fish genome, the artificial transposon Frog prince which is derived from frog and the transposon PiggyBac which is derived from insect.

As the transposase, a native enzyme may be used, and any transposase in which a part of its amino acids are substituted, deleted, inserted and/or added may be used as long as the same transfer activity as the transposase is maintained. By controlling the enzyme activity of the transposase, the transfer reaction of the DNA existing between the transposon sequences can be controlled.

In order to analyze whether or not it possesses a transfer activity similar to that of transposase, it can be measured by the 2-components analyzing system disclosed in Japanese Published Unexamined Patent Application No. 235575/2003.

Illustratively, whether or not a non-automatic Tol2 element can be transferred and inserted into a mammalian cell chromosome by the activity of a transposase can be analyzed by separately using a plasmid comprising a Tol2 transposase-deleted Tol2 transposon (Tol2-derived non-autonomous transposon) and a plasmid comprising Tol2 transposase.

The term "non-autonomous transposon" in the present specification means a transposon which is lost a transposase existed inside the transposon and cannot therefore perform its autonomous transfer. The non-autonomous transposon can transfer the DNA inserted between transposon sequences of the non-autonomous transposon into the host cell chromosome, by allowing a transposase protein, an mRNA encoding the transposase protein or a DNA encoding the transposase protein to simultaneously present in the cell.

The transposase gene means a gene encoding a transposase. In order to improve its expression efficiency in a mammalian cell, a sequence which adjusts a space between the Kozak's consensus sequence (Kozak M., *Nucleic Acids Res.*, 12, 857-872 (1984)) or a ribosome binding sequence, Shine-Dalgarno sequence and the initiation codon, to an appropriate distance (e.g., from 6 to 18 bases) may be connected to an upstream site of the translation initiation codon ATG of the gene.

According to the method of the invention, in order to integrate a gene fragment comprising a DNA encoding the protein of interest and a selectable marker gene in an expression vector into the chromosome of a host cell, an expression vector which comprises the gene fragment comprising a DNA encoding the protein of interest and a selectable marker gene and transposon sequences at both terminals of the gene fragment is introduced into the host cell, and a transposase is allowed to act upon the transposon sequences comprised in the expression vector which is introduced into the cell.

In order to allow a transposase to act upon the transposon sequences comprised in the expression vector which is introduced into the cell, the transposase may be injected into the cell, or an expression vector comprising a DNA encoding the transposase may be introduced into the host cell together with an expression vector comprising a DNA encoding the protein of interest and a selectable marker gene. In addition, by introducing an RNA encoding a transposase gene into the host cell, the transposase may be expressed in the cell.

The expression vector is not particularly limited. Any expression vector can be used by optionally selecting from the expression vectors known to those skilled in the art, depending on a host cell into which an expression vector comprising a transposase gene is introduced; the use; and the like.

In order that a protein constituted from two or more polypeptides is produced by the method of the invention, the DNA can be integrated into the chromosome of the cell by integrating a DNA encoding the two or more polypeptides into the same or different expression vectors and then introducing the expression vectors into a host cell.

The transposase may be inserted into an expression vector to express together with the protein of interest or may be inserted into a vector different from the expression vector. The transposase may be allowed to act transiently or may be allowed to act continuously, but it is preferably to allow the transposase to act transiently in order to prepare a cell for stable production.

As the method for allowing the transposase to act transiently, examples include a method comprising preparing an expression vector which comprises a DNA encoding the transposase and an expression vector comprising a DNA encoding a protein of interest and then introducing both of the expression plasmids simultaneously into a host cell.

The term "expression vector" in the present specification means an expression vector to be used for introducing a mammalian cell in order to express a protein of interest. The expression vector used in the invention has a structure in which at least a pair of transposon sequences is present at both sides of an expression cassette.

The term "expression cassette" in the present specification means a nucleotide sequence which has a gene expression controlling region necessary for expressing a protein of interest and a sequence encoding the protein of interest. Examples of the gene expression controlling region include an enhancer, a promoter, and a terminator. the expression cassette may contain a selectable marker gene.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter, moloney murine leukemia virus, an enhancer and the like. Also, the enhancer of the IE gene of human CMV can be used together with the promoter.

The "selectable marker gene" means an arbital other marker gene which can be used for distinguishing a cell to which a plasmid vector is introduced from a cell lacking of the vector.

Examples of the selectable marker gene include a drug resistance gene (a neomycin resistance gene, a DHFR gene, a puromycin resistance gene, a blasticidin resistance gene, a hygromycin resistance gene, and a cycloheximide resistance gene (Japanese Published Unexamined Patent Application No. 262879/2002)), fluorescence and bio-luminescence marker genes (such as green fluorescent protein GFP) and the like.

In the invention, preferable selectable marker is a drug resistance gene and particularly preferable selectable marker is a cycloheximide resistance gene. In addition, by carrying out a gene modification of the selectable marker gene, drug resistance performance and luminescence performance of the selectable marker protein can also be modified.

Cycloheximide (hereinafter sometimes referred to as CHX) is a protein synthesis inhibitor, and as examples of the use of the CHX resistance gene as a selectable marker gene, the cases of yeast (Kondo K. *J. Bacteriol.*, 177, 24, 7171-7177 (1995)) and animal cells (Japanese Published Unexamined Patent Application No. 262879/2002) are known.

In the case of the animal cells, it has been found that the resistance to cycloheximide is provided by a transformant which expresses a protein encoded by the nucleotide sequence shown in SEQ ID NO:7 of Sequence Listing in which proline at position 54 in human ribosomal protein subunit L36a encoded by the nucleotide sequence shown in SEQ ID NO:5 of Sequence Listing is substituted with glutamine.

The method for introducing the above-mentioned protein expression vector comprising a transposon sequence, a transposase expressing plasmid vector and RNA is not particularly limited. Examples include calcium phosphate transfection, electroporation, a liposome method, a gene gun method, lipofection and the like.

Examples of the method for directly introducing a transposase in the form of a protein include by microinjection or endocytosis for supplying into a cell. The gene transfer can be carried out by the method described in *Shin Idenshi Kogaku Handbook* (New Genetic Engineering Handbook), edited by Masami Muramatsu and Tadashi Yamamoto, published by Yodo-sha, ISBN 9784897063737.

The host cell may be any mammalian cell as long as it can be subcultured and stably express a protein of interest. Examples of the host cell include PER.C6 cell, human leukemia cell Namalwa cell, monkey cell COS cell, rat myeloma cell YB2/3HL.P2.G11.16Ag.20 (also referred to as YB2/0), mouse myeloma cell NS0, mouse myeloma cell SP2/0-Ag14, Syrian hamster cell BHK, HBT5637 (Japanese Unexamined Patent Application Publication No. 1998-000299), Chinese hamster ovarian cell CHO cell (*Journal of Experimental Medicine*, 108, 945 (1958); *Proc. Natl. Acad. Sci. USA.*, 601275 (1968); *Genetics*, 55, 513 (1968); *Chromosoma*, 41, 129 (1973); *Methods in Cell Science*, 18, 115 (1996); *Radiation Research*, 148, 260 (1997); *Proc. Natl. Acad. Sci. USA.*, 77, 4216 (1980); *Proc. Natl. Acad. Sci.*, 60, 1275 (1968); *Cell*, 6, 121 (1975); *Molecular Cell Genetics, Appendix I,II* (pp. 883-900)), CHO/DG44, CHO-K1 (ATCC CCL-61), DUKXB11 (ATCC CCL-9096), Pro-5 (ATCC CCL-1781), CHO-S (Life Technologies, Cat #11619), Pro-3 and substrain of CHO cell.

In addition, the above-mentioned host cell can also be used in the protein production method of the invention by modifying it so as to be suitable for the protein production, by modification of chromosomal DNA, introduction of an exogeneous gene, and the like.

Further, in order to control the sugar chain structure bound to a protein of interest to be produced, Lec13 which acquired lectin resistance [*Somatic Cell and Molecular Genetics*, 12, 55 (1986)] and CHO cell from which α1,6-fucosyltransferase gene is deleted (WO2005/35586, WO2002/31140) can also be used as the host cell.

The protein of interest may be any protein so long as it can be expressed by the method of the invention. Specifically, examples include a human serum protein, a peptide hormone, a growth factor, a cytokine, a blood coagulation factor, a fibrinolysis system protein, an antibody and partial fragments of various proteins, and the like.

Preferable examples of the protein of interest include a monoclonal antibody such as a chimeric antibody, a humanized antibody and a human antibody; Fc fusion protein; and albumin-bound protein; and a fragment thereof.

An effector activity of a monoclonal antibody obtained by the method of the present invention can be controlled by various methods. For example, known methods are a method for controlling an amount of fucose (hereinafter, referred to also as "core fucose") which is bound N-acetylglucosamine (GlcNAc) through α-1,6 bond in a reducing end of a complex type N-linked sugar chain which is bound to asparagine (Asn) at position 297 of an Fc region of an antibody (WO2005/035586, WO2002/31140, and WO00/61739), a method for controlling an effector activity of a monoclonal antibody by modifying amino acid group(s) of an Fc region of the antibody, and the like. The effector activity of the monoclonal antibody produced by the method of the present invention can be controlled by using any of the methods.

The "effector activity" means an antibody-dependent activity which is induced via an Fc region of an antibody. As the effector activity, an antibody-dependent cellular cytotoxicity (ADCC activity), a complement-dependent cytotoxicity (CDC activity), an antibody-dependent phagocytosis (ADP activity) by phagocytic cells such as macrophages or dendritic cells, and the like are known.

In addition, by controlling a content of core fucose of a complex type N-linked sugar chain of Fc region of a monoclonal antibody, an effector activity of the antibody can be increased or decreased.

As a method for lowering a content of fucose which is bound to a complex type N-linked sugar chain bound to Fc of the antibody, an antibody to which fucose is not bound can be obtained by the expression of an antibody using a CHO cell which is deficient in a gene encoding α1,6-fucosyltransferase. The antibody to which fucose is not bound has a high ADCC activity.

On the other hand, as a method for increasing a content of fucose which is bound to a complex type N-linked sugar chain bound to Fc of an antibody, an antibody to which fucose is bound can be obtained by the expression of an antibody using a host cell into which a gene encoding α1,6-fucosyltransferase is introduced. The antibody to which fucose is bound has a lower ADCC activity than the antibody to which fucose is not bound.

Further, by modifying amino acid residue(s) in an Fc region of an antibody, the ADCC activity or CDC activity can be increased or decreased. For example, the CDC activity of an antibody can be increased by using the amino acid sequence of the Fc region described in US2007/0148165.

Further, the ADCC activity or CDC activity of an antibody can be increased or decreased by modifying the amino acid as described in U.S. Pat. No. 6,737,056, or 7,297,775 or 7,317,091.

The term "suspension mammalian cell" in the present invention means a cell which does not adhere to a cell culture anchorage coated for facilitating adhesion of culture cells, such as microbeads, a culture container for tissue culture (also referred to as a tissue culture or adhesion culture container and the like) and the like, and can survive and grow by suspending in the culture liquid.

When the cell does not adhere to the cell culture anchorage, it may survive and grow under a state of a single cell in the culture liquid or survive and grow under a state of a cell mass formed by the agglutination of two or more cells.

In addition, as the suspension mammalian cell to be used in the present invention, a cell which can survive and grow in a serum-free medium that does not contain fetal calf serum (hereinafter referred to as FCS) and the like, while suspending in the culture liquid without adhering to the cell culture anchorage, is preferable, and a mammalian cell which can survive and grow while suspending in a protein-free medium that does not contain protein is more preferable.

As the culture container for tissue culture, it may be any culture container such as a flask, a Petri dish and the like, so long as coating for adhesion culture is applied thereto. Specifically, for example, whether or not it is a suspension mammalian cell can be confirmed by the use of commercially available tissue culture flask (manufactured by Greiner), adhesion culture flask (manufactured by Sumitomo Bakelite) and the like.

As the suspension mammalian cell to be used in the present invention, it may be either a cell prepared by further adapting a cell originally having a suspension property to suspension culture or a suspension mammalian cell prepared by adapting an adhesive mammalian cell to suspension culture conditions.

Examples of the cell originally having a suspension property include PER.C6 cell, a rat myeloma cell YB2/3HL.P2.G11.16Ag.20 (or also called YB2/0), CHO-S cell (manufactured by Invitrogen) and the like.

The aforementioned "suspension mammalian cell prepared by adapting an adhesive mammalian cell to suspension culture conditions" can be prepared by the method described in *Mol. Biotechnol.*, 2000, 15(3), 249-57 or by the method shown in the following, and can be prepared by establishing a cell which shows proliferation property and surviving property similar to those before the suspension culture adaptation or superior to those before adapting to suspension culture (*J. Biotechnol.*, 2007, 130(3), 282-90).

The term "similar to those before the suspension culture adaptation" means that survival ratio, proliferation rate (doubling time) and the like of the cell adapted to the suspension culture are substantially the same as those of the cell before adapting suspension culture.

Examples of the method for adapting an adhesive mammalian cell to suspension culture conditions according to the present invention include the following method. The serum content of a serum-containing medium is reduced to 1/10 and sub-culturing is repeated at relatively high concentration of cell. When the mammalian cell comes to be able to survive and proliferate, the serum content is further reduced and the sub-culturing is repeated. By this method, a suspension mammalian cell which can survive and proliferate under serum-free conditions can be prepared.

In addition, a suspension mammalian cell can also be prepared by a method comprising culturing with the addition of an appropriate nonionic surfactant such as Pluronic-F68 or the like in the culture liquid.

Examples of the adhesive mammalian cell which acquires suspension property by adapting to a suspension culture condition include a mouse myeloma cell NS0, a CHO cell and the like.

In the present invention, as a property possessed by the suspension mammalian cell, when $2\times10^5$ cells/ml of the cell is suspension-cultured, the cell concentration after culturing for 3 or 4 days is preferably $5\times10^5$ cells/ml or more, more preferably $8\times10^5$ cells/ml or more, particularly preferably $1\times10^6$ cells/ml or more, most preferably $1.5\times10^6$ cells/ml or more.

In addition, doubling time of the suspension mammalian cell of the present invention is preferably 48 hours or less, more preferably 24 hours or less, particularly preferably 18 hours or less, most preferably 11 hours or less.

Examples of the medium for suspension culturing include commercially available media, such as CD-CHO medium (manufactured by Invitrogen), EX-CELL 325-PF medium (manufactured by SAFC Biosciences), SFM4CHO medium (manufactured by HyClone) and the like. In addition, it can also be obtained by mixing saccharides, amino and the like acids which are necessary for the culturing of mammalian cells.

The suspension mammalian cell can be cultured using a culture container which can be used for suspension culturing under a culture condition capable of suspension culturing. Examples of the culture container include a 96 well plate for cell culture (manufactured by Corning), a T-flask (manufactured by Becton Dickinson), an Erlenmeyer flask (manufactured by Corning) and the like.

Regarding the culture conditions, for example, it can be statically cultured in an atmosphere of 5% $CO_2$ at a culture temperature of 37° C. A shaking culture equipment, such as culturing equipment for suspension culture exclusive use, Wave Bioreactor (manufactured by GE Healthcare Bioscience), can also be used.

Regarding the suspension culture conditions of a suspension mammalian cell using the Wave Bioreactor equipment, the cell can be cultured by the method described on the GE Healthcare Bioscience homepage www.gelifesciences.co.jp/tech-support/manual/pdf/cellcult/wave-03-16.pdf.

In addition to the shaking culture, culturing by a rotation agitation equipment such as a bioreactor, can also be used. Culturing using a bioreactor can be carried out by the method described in *Cytotechnology*, (2006) 52: 199-207, and the like.

In the present invention, when a cell line other than the suspension mammalian cells is used, any cell line can be used so long as it is a mammalian cell line adapted to the suspension culture by the above-mentioned method and is a cell line which can be used in the protein producing method of the present invention.

Purification of the protein of interest produced by the suspension mammalian cell is carried out by separating the protein of interest from impurities other than the protein of interest in a culture liquid or cell homogenate containing the protein of interest. Examples of the separation method include centrifugation, dialysis, ammonium sulfate precipitation, column chromatography, a filter and the like. The separation can be carried out based on the difference in physicochemical properties of the protein of interest and impurities and based on the difference in their affinity for the column carrier.

The method for purifying the protein of interest can be carried out, for example, by the method described in *Protein Experimentation Note* (the first volume)—*Extraction, Separation and Expression of Recombinant Protein* (translation of a textbook written in Japanese) (edited by Masato Okada and Kaori Miyazaki, published by Yodo-sha, ISBN 9784897069180).

The entire contents of the references, such as the scientific documents, patents, patent applications cited herein are incorporated herein by reference to the same degree of those illustratively described, respectively.

The present invention has been described in the foregoing by showing preferred embodiments thereof for the sake of easy understanding. Hereinafter, the present invention is further described specifically based on examples, but the above-mentioned explanations and the following examples are provided merely for the purpose of exemplifications and not provided for the purpose of limiting the invention. Accordingly, the scope of the invention is not limited to the embodiments and examples which are specifically described herein, but is limited by the claims alone.

Various experimental techniques relating to genetic recombination described hereinafter, such as the cloning and the like were carried out in accordance with the genetic engineering techniques described in *Molecular Cloning* 2$^{nd}$ edition edited by J. Sambrook, E. F. Frisch and T. Maniatis, *Current Protocols in Molecular Biology* edited by Frederick M. Ausubel et al, published by Current Protocols, and the like.

By the method for producing the protein of the present invention, a protein of interest can be efficiently produced using a suspension mammalian cell. The cell of the present invention can be used as a protein producing cell for producing a recombinant protein.

EXAMPLES

Example 1

Preparation of Transposon Vector for Expressing Anti-Human Influenza M2 Antibody A plasmid which contains a gene expression cassette for mammalian cells comprising an arbitrary human antibody gene and a drug resistance marker gene inserted between a pair of Tol2 transposon sequences was used as a plasmid vector for protein expression.

Each DNA of the used genes was chemically and artificially synthesized based on a known nucleotide sequence or obtained by preparing primers for its both terminal sequences and then carrying out PCR using an appropriate DNA source as a template. In order to carry out the gene manipulation later, a restriction site for a restriction enzyme was added to the terminal of the primer.

Among the nucleotide sequence of the non-autonomous Tol2 transposone disclosed by Japanese Published Unexamined Patent Application No. 235575/2003 (SEQ ID NO:1), the nucleotide sequence at position 1 to 200 (Tol2-L sequence) (SEQ ID NO:2) and the nucleotide sequence at positions 2285 to 2788 (Tol2-R sequence) (SEQ ID NO:3) were used as the transposon sequences.

Each synthetic DNA fragments comprising a pair of transposon sequences (manufactured by TAKARA BIO INC.) was prepared by the following method. A DNA fragment comprising a nucleotide sequence in which a recognition sequence of a restriction enzyme NruI was attached to both of the 5'-terminal and 3'-terminal of the Tol2-R sequence was prepared. Then, a DNA fragment comprising a nucleotide sequence in which a recognition sequence of a restriction enzyme FseI was attached to the 5'-terminal of the Tol2-L sequence and a restriction enzyme AscI was attached to the 3'-terminal thereof was prepared.

Next, the thus prepared DNA fragments comprising Tol2-R sequence and Tol2-L sequence were inserted into an expression vector N5LG1-M2-Z3 vector (WO2006/061723) comprising a nucleotide sequence encoding an amino acid sequence of anti-human influenza M2 antibody Z3G1.

The N5LG1-M2-Z3 vector (WO2006/061723) into which a nucleotide sequence (SEQ ID NO:8) encoding the H chain of the anti-human influenza M2 antibody Z3G1 (ATCC Deposit No. PTA-5968: deposited Mar. 13, 2004, American Type Culture Collection, Manassas, Va., USA) and a nucleotide sequence (SEQ ID NO:10 and SEQ ID NO:11) encoding the L chain (SEQ ID NO:9) of the same were inserted under the control of the CMV enhancer/promoter control was used as an antibody gene expression cassette.

The DNA fragment comprising the Tol2-R sequence was inserted into the restriction enzyme NruI site of the N5LG1-M2-Z3 vector, at the 5'-terminal side of a gene fragment comprising the antibody gene expression cassette and a resistance marker gene. Then, the DNA fragment comprising the Tol2-L sequence was inserted into the restriction enzyme FseI and AscI sites at the 3'-terminal side.

Figure 1:
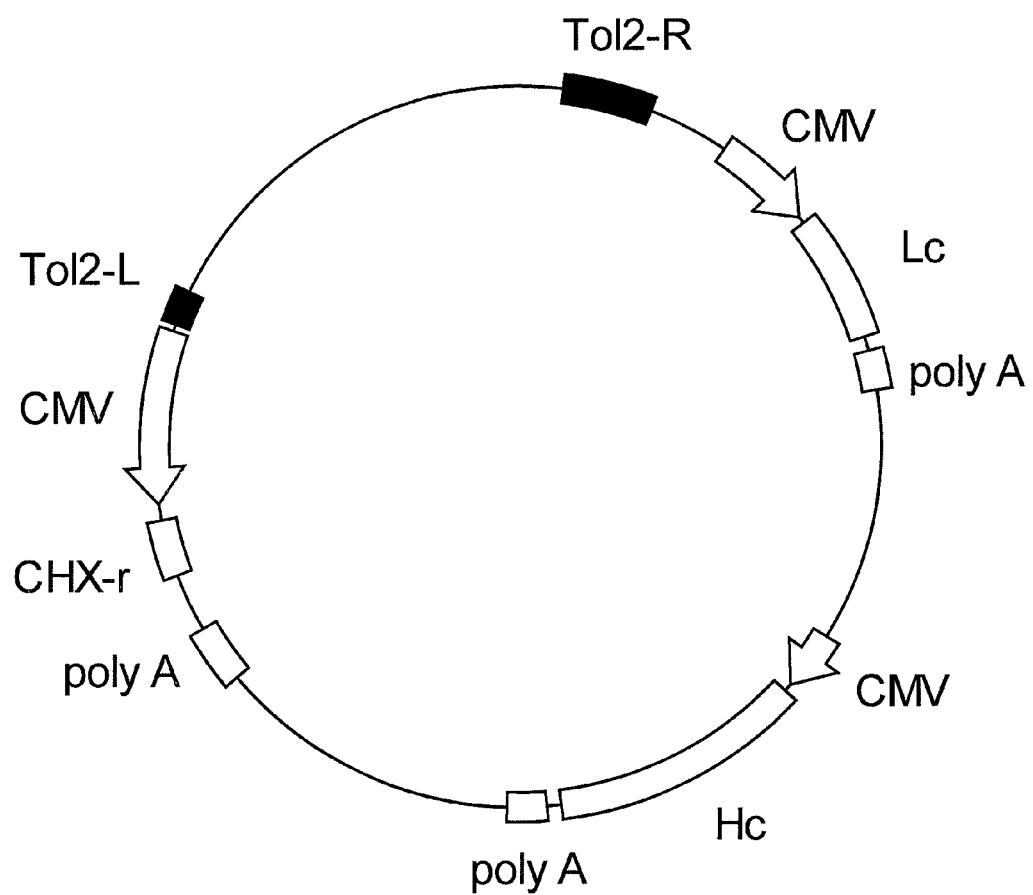
FIG. 1 shows a schematic illustration of a transposon vector for expressing an anti-human influenza M2 antibody.

In addition, a transposon vector for expressing an anti-human influenza M2 antibody was constructed (FIG. 1) by inserting a cycloheximide resistance gene expression cassette connected with a nucleotide sequence (SEQ ID NO:5) encoding a resistance gene for cycloheximide (a gene in which proline at position 54 of the human ribosomal protein L36a was substituted with glutamine) into the FseI recognition site of the N5LG1-M2-Z3 vector connected with the Tol2 transposon sequence, under the control of the CMV enhancer/promoter.

On the other hand, a vector containing no transposon sequences was named anti-human influenza M2 antibody expression vector and used as the control vector (FIG. 2).

Example 2

Preparation of Transposase Expression Vector

The transposase was expressed using an expression vector independent of the expression vector of the antibody of interest. That is, a gene which is encoding a medaka fish-derived Tol2 transposase (SEQ ID NO:4) was inserted into a downstream of the CAGGS promoter of a pCAGGS vector (*Gene*, 108, 193-200, 1991) and used as the expression vector (FIG. 3).

Example 3

(1) Preparation of Suspension CHO Cell

An adhesive CHO cell which had been cultured using an α-MEM medium (manufactured by Invitrogen) containing 10% serum (FCS) was peeled off and recovered by a trypsin treatment and shaking-cultured at 37° C. in a 5% $CO_2$ incubator using fresh α-MEM medium containing 10%

FCS. Several days thereafter, growth of these cells was confirmed and then shaking culture was carried out by seeding them into a α-MEM medium containing 5% FCS at a concentration of $2 \times 10^5$ cells/ml.

Further several days thereafter, the inoculation was similarly carried out using the α-MEM medium containing 5% FCS. Finally, a cell adapted to the suspension culture was prepared by repeating the sub-culture and shaking culture using serum-free α-MEM medium and confirming that the cells have the same growing ability of the case of their culturing in the presence of serum.

(2) Preparation of Antibody-Producing CHO Cell

The transposon vector for expressing the anti-human influenza M2 antibody prepared in Example 1 and Example 2 (hereinafter referred to as transposon vector) and Tol2 transposase expression vector pCAGGS-T2TP (FIG. 3, Kawakami K. & Noda T., Genetics, 166, 895-899 (2004)) were used as the expression vectors. In addition, the anti-human influenza M2 antibody expression vector having no transposon sequences was used as the control.

By introducing the aforementioned expression vectors into the suspension culture-adapted CHO-K1 cell (American Type Culture Collection Cat. No. CCL-61) or HEK293 cell (FreeStyle 293F cell, manufactured by Invitrogen), the frequencies of obtaining cycloheximide-resistant clones were compared.

Each cells ($4 \times 10^6$ cells) was suspended in 400 μl of PBS, and the transposon vector for expressing the anti-human influenza M2 antibody (10 μg) and Tol2 transposase expression vector (25 μg) were co-transfected directly in the form of circular DNA by electroporation. In this connection, in order to express the Tol2 transposase transiently, the Tol2 transposase expression vector was directly introduced in the form of circular DNA for the purpose of preventing from integrateing into the host chromosome.

In addition, as the control, the anti-human influenza M2 antibody expression vector (10 μg) was linearized by a restriction enzyme and then introduced into each cells, in accordance with the standard gene transfer method by electroporation.

The electroporation was carried out using a cuvette of 4 mm in gap width (manufactured by Bio-Rad®), using an electroporator (Gene Pulser Xcell™ System (manufactured by Bio-Rad®)) under conditions of 300 V in voltage, 500 μF in electrostatic capacity and room temperature.

After the transfection by electroporation, each cell was seeded into three 96-well plates and cultured in a $CO_2$ incubator for 3 days using the EX-CELL 325-PF medium manufactured by SAFC Biosciences for the CHO cell, and the FreeStyle-293 medium (manufactured by Invitrogen) for the HEK293 cell.

Next, from the day of medium exchange on the 4th day of the transfection, 3 μg/ml of cycloheximide was added to the medium so that the cells were cultured in the presence of cycloheximide, followed by culturing for 3 weeks while carrying out the medium exchange in every week.

After culturing for 3 weeks, the number of wells in which cycloheximide-resistant colonies were found was counted. The results are shown in Table 1 and Table 2.

TABLE 1

Comparison of the numbers of cycloheximide-resistant cells (CHO cell)

|  | Transposon vector | Conventional vector |
|---|---|---|
| Test 1 | 155/288 | 0/288 |
| Test 2 | 100/288 | 0/288 |
| Test 3 | 94/288 | 0/288 |

TABLE 2

Comparison of the numbers of cycloheximide-resistant cells (HEK293 cell)

|  | Transposon vector | Conventional vector |
|---|---|---|
| Test 1 | 0/288 | 0/288 |
| Test 2 | 0/288 | 0/288 |
| Test 3 | 0/288 | 0/288 |

As shown in Table 1, each the anti-human influenza M2 antibody expression transposon vector or anti-human influenza M2 antibody expression vector was introduced into the suspension CHO-K1 cell. As a result, cycloheximide-resistant transformants were not obtained from the cell introduced with anti-human influenza M2 antibody expression vector like the case of other cell lines, but cycloheximide-resistant transformants were obtained from the cell introduced with transposon vector for expressing anti-human influenza M2 antibody with a high frequency.

On the other hand, as shown in Table 2, cycloheximide-resistant transformants were not obtained when either of the transposon vector for expressing anti-human influenza M2 antibody and anti-human influenza M2 antibody expression vector was introduced into the HEK293 cell.

Based on these results, it was found that the intended protein-encoded gene and cycloheximide resistance gene which were inserted between a pair of transposon sequences are efficiently introduced into the chromosome of the host cell, namely a suspension mammalian cell.

(3) Examination on the Antibody Production by Suspension CHO Cell and Adhesive CHO Cell In order to examine antibody production efficiency by a suspension CHO cell or an adhesive CHO cell, the amounts of antibodies produced by respective cell lines were examined. As the suspension CHO cell, the suspension CHO-K1 cell adapted to suspension culture was used. In addition, as the adhesive CHO cell, the adhesive CHO-K1 cell before adaptation to suspension culture was used.

The anti-human influenza M2 antibody expression transposon vector (10 μg) and Tol2 transposase expression vector (25 μg) were introduced into the suspension CHO-K1 cell and adhesive CHO-K1 cell by means of electroporation, respectively. Thereafter, the suspension CHO-K1 cell and the adhesive CHO-K1 cell were seeded into three 96-well plates for each cell.

A medium for suspension cells (EX-CELL 325-PF, manufactured by SAFC Biosciences) was used for the suspension CHO-K1 cell, and the α-MEM medium containing 10% serum was used for the adhesive CHO-K1 cell. Each cell was cultured in a $CO_2$ incubator for 3 days. From the day of medium exchange on the 4th day of the transfection, 3 μg/ml of cycloheximide was added to the medium so that the cells were cultured in the presence of cycloheximide and the cells were further cultured for 3 weeks. In this case, the medium exchange was carried out every week.

For the suspension CHO-K1 cell, $1 \times 10^6$ of the cells were seeded into a 6-well plate and shaking-cultured in a $CO_2$ incubator for 3 days, and the amount of the anti-human influenza M2 antibody protein was measured by HPLC using the culture supernatant.

For the adhesive CHO-K1 cell, medium exchange was carried out when the cell reached confluent on a 6-well plate ($2 \times 10^6$ cells), and 3 days after static culture, the amount of the antibody protein was measured by HPLC using the culture supernatant.

The antibody concentration in the culture supernatant was measured in accordance with the method described in Yeast Res., 7 (2007), 1307-1316. The results are shown in FIG. 4A and FIG. 4B.

As shown in FIG. 4A, a large number of cells showing a markedly high antibody expression level were obtained when the CHO-K1 cell adapted to suspension culture was used. On the other hand, as shown in FIG. 4B, only the cells showing an expression level of the HPLC detection limit (5 μg/ml) or less were obtained when the adhesive CHO-K1 cell was used.

Based on these results, it was found that, for the expression of a protein of interest using a transposon vector, the protein of interest can be expressed at a high level when a suspension mammalian cell is used.

In addition, it was found from the results of Examples 1 to 3 that the method of the invention can be used as a novel method for producing a protein of interest, by efficiently preparing a production cell which can highly express an exogeneous gene using a suspension mammalian cell adapted to suspension culture.

Example 4

Preparation of Tol1 Transposon Vector for Expressing Anti-Human Influenza M2 Antibody In the same manner as in Example 1, a plasmid which contains a gene expression cassette for mammalian cells, comprising an arbitrary human antibody gene and a drug resistance marker gene inserted between a pair of Tol1 transposon sequences, was used as a protein expression plasmid vector.

Each DNA of the used genes was chemically synthesized artificially based on the known sequence information or obtained by preparing primers of its both terminal sequences and carrying out PCR using an appropriate DNA source as the template. For the gene manipulation to be carried out later, a site cleaved by a restriction enzyme was added to the end of the primer.

Among the non-autonomous Tol1 transposon nucleotide sequence shown in SEQ ID NO:13 of Sequence Listing (WO2008/072540), the nucleotide sequence at positions 1 to 200 (Tol1-L sequence) (SEQ ID NO:14) and the nucleotide sequence at positions 1351 to 1855 (Tol1-R sequence) (SEQ ID NO:15) were used as the transposon sequences.

Each of the synthetic DNA fragments comprising each a pair of transposon sequences was prepared by the following method. A DNA fragment comprising a nucleotide sequence in which a recognition sequence of a restriction enzyme NruI was connected to both of the 5'-terminal and 3'-terminal of the Tol1-R sequence. Then, a DNA fragment comprising a nucleotide sequence in which a recognition sequence of a restriction enzyme FseI was connected to the 5'-terminal of the Tol1-L sequence and a restriction enzyme AscI was connected to the 3'-terminal thereof.

Next, the thus prepared DNA fragments comprising Tol1-R sequence and Tol1-L sequence were inserted into the expression vector N5LG1-M2-Z3 vector. The DNA fragment comprising the Tol1-R sequence was inserted into the restriction enzyme NruI site of the N5LG1-M2-Z3 vector, existing on the 5'-terminal side of a gene fragment comprising the antibody gene expression cassette and a resistance marker gene, and the DNA fragment comprising the Tol1-L sequence was inserted into the restriction enzyme FseI and AscI sites existing on the 3'-terminal side.

In addition, Tol1 transposon vector for expressing an anti-human influenza M2 antibody was constructed (FIG. 5) by inserting a cycloheximide resistance gene expression cassette connected with a resistance gene for cycloheximide (a gene in which proline at position 54 in the human ribosomal protein L36a was mutated to glutamine) into the FseI recognition site of the N5LG1-M2-Z3 vector connected with the Tol1 transposon sequence, under the control of the CMV enhancer/promoter.

Example 5

Preparation of Tol1 Transposase Expression Vector

The transposase was expressed using an expression vector independent from the expression vector of the antibody of interest. That is, a Tol1 transposase gene expression cassette connected with a DNA fragment encoding a medaka fish-derived Tol1 transposase, containing the nucleotide sequence shown in SEQ ID NO:16 of Sequence Listing, was inserted into pBluescriptII SK (+) (manufactured by Stratagene) under the CMV enhancer/promoter control and used as the expression vector pTol1ase (FIG. 6).

Example 6

(1) Preparation of Antibody-Producing CHO Cell

The Tol1 transposon vector for expressing the anti-human influenza M2 antibody (hereinafter referred to as Tol1 transposon vector) and Tol1 transposase expression vector pTol1ase of Example 4 and Example 5 were used as the expression vectors. In addition, the CHO-K1 cell prepared by adapting to suspension culture in the same manner as in Example 3(1) was used as the cell.

The aforementioned expression vectors were introduced into the CHO-K1 cell adapted to suspension culture, and the frequency of obtaining clones resistant to cycloheximide was measured. The CHO-K1 cell adapted to suspension culture ($4\times10^6$ cells) were suspended in 400 μl of PBS, and the Tol1 transposon vector for expressing the anti-human influenza M2 antibody (10 μg) and Tol1 transposase expression vector (50 μg) were co-transfected directly in the form of circular DNA by electroporation. In order to effect transient expression of the Tol1 transposase, the Tol1 transposase expression vector was directly introduced in the form of circular DNA for the purpose of preventing from integrating into the host chromosome.

The electroporation was carried out using a cuvette of 4 mm in gap width (manufactured by Bio-Rad®), using an electroporator (Gene Pulser Xcell™ System (manufactured by Bio-Rad®)) under conditions of 300 V in voltage, 500 μF in electrostatic capacity and room temperature.

After the transfection by electroporation, each cell was seeded into two 96-well plates and cultured in a $CO_2$ incubator for 3 days using the EX-CELL 325-PF medium (manufactured by SAFC Biosciences) for the CHO cell. Next, from the day of medium exchange on the 4th day of the transfection, 3 μg/ml of cycloheximide was added to the medium so that the cells were cultured in the presence of cycloheximide, followed by culturing for 3 weeks while carrying out the medium exchange every week.

After the culturing for 3 weeks, the number of wells in which cycloheximide-resistant colonies were found was counted. The results are shown in Table 3. Each of the tests 1 to 3 in Table 3 shows a result of carrying out the gene transfer three times.

TABLE 3

|  | Tol1 transposon vector |
| --- | --- |
| Tests 1 | 133/192 |
| Tests 2 | 67/192 |
| Tests 3 | 122/192 |

As shown in Table 3, when the Tol1 transposon vector for expressing the anti-human influenza M2 antibody was introduced into the suspension CHO-K1 cell, cycloheximide-resistant transformants were obtained at a high frequency similarly to Example 3 in which the Tol2 transposon vector for expressing the anti-human influenza M2 antibody was introduced.

It was found based on these results that the antibody gene and cycloheximide resistance gene inserted between a pair of transposon sequences are efficiently transduced into the chromosome of the host cell, namely the suspension mammalian cell, in the case of using the Tol1 transposon, too.

(2) Examination on Antibody Production by Suspension CHO-K1 Cell

Antibody production efficiency of the suspension CHO-K1 cell was examined using the suspension CHO-K1 cell. The transposon vector for expressing the anti-human influenza M2 antibody (10 μg) and Tol1 transposase expression vector (50 μg) were introduced by electroporation into the suspension CHO-K1 cell adapted to suspension culture.

Thereafter, the cells were seeded into respective two 96-well plates and cultured for 3 days in a $CO_2$ incubator using the suspension culture medium EX-CELL 325-PF. From the medium exchange on the 4th days after the electroporation, the cells were cultured for 3 weeks in the presence of 3 μg/ml of cycloheximide. In this case, the medium exchange was carried out every week.

For the suspension CHO-K1 cell, $1 \times 10^6$ of the cells were seeded into a 6-well plate and shaking-cultured in a $CO_2$ incubator for 3 days, and amount of the anti-human influenza M2 antibody protein was measured by HPLC using the culture supernatant.

The antibody concentration in culture supernatant was measured in accordance with the method described in *Yeast Res.*, 7 (2007), 1307-1316. The results are shown in FIG. 7.

As shown in FIG. 7, a large number of cells showing a markedly high antibody expression level were obtained in the case of the use of the Tol1 transposon, too. From this result, it was found that similar to the case of the use of the Tol2 transposon-derived nucleotide sequence, a suspension mammalian cell capable of highly expressing the protein of interest can also be obtained when a Tol1 transposon-derived nucleotide sequence is used as the transposon sequence.

While the invention has been described in detail and with reference to specific embodiments thereof, it will be apparent to one skill in the art that various changes and modifications can be made therein without departing from the spirit and scope thereof.

This application is based on Japanese application No. 2009-140626, filed on Jun. 11, 2009, and U.S. provisional application No. 61/186,138, filed on Jun. 11, 2009, the entire contents of which are incorporated hereinto by reference. All references cited herein are incorporated in their entirety.

What is claimed is:

1. (I) A method for producing an antibody or an antibody fragment thereof, comprising introducing an expression vector which comprises a gene fragment comprising a DNA encoding an antibody or an antibody fragment thereof and a selectable marker gene, and transposon sequences at both terminals of the gene fragment, into a suspension mammalian cell; integrating the gene fragment inserted between a pair of the transposon sequences, into a chromosome of the mammalian cell to obtain a mammalian cell capable of expressing the antibody or the antibody fragment thereof; and suspension-culturing the mammalian cell;

(II) a method for producing an antibody or an antibody fragment thereof, which comprises the following steps (A) to (C):

(A) a step of simultaneously introducing the following expression vectors (a) and (b) into a suspension mammalian cell (a) an expression vector which comprises a gene fragment comprising a DNA encoding an antibody or an antibody fragment thereof, and transposon sequences at both terminals of the gene fragment, (b) an expression vector which comprises a DNA encoding a transposase which recognizes the transposon sequences and has activity of transferring the gene fragment inserted between a pair of the transposon sequences into a chromosome, (B) a step of transiently expressing the transposase from the expression vector introduced in step (A) to integrate the gene fragment inserted between a pair of the transposon sequences into a chromosome of the mammalian cell, to obtain a suspension mammalian cell capable of expressing the antibody or the antibody fragment thereof, and (C) a step of suspension-culturing the suspension mammalian cell capable of expressing the antibody or the antibody fragment thereof obtained in step (B) to produce the antibody or the antibody fragment thereof; or (III) a method for obtaining a suspension mammalian cell capable of expressing an antibody or an antibody fragment thereof, comprising introducing an expression vector which comprises a gene fragment comprising a DNA encoding an antibody or an antibody fragment thereof and a selectable marker gene, and transposon sequences at both terminals of the gene fragment, into a suspension mammalian cell; and integrating the gene fragment inserted between a pair of the transposon sequences, into a chromosome of the mammalian cell, wherein in the methods of (I)-(III), a pair of the transposon sequences are nucleotide sequences derived from a pair of Tol1 transposons or nucleotide sequences derived from a pair of Tol2 transposons and the suspension mammalian cell is at least one selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension-culture.

2. The method according to claim 1,
(I) wherein the suspension mammalian cell is a cell capable of surviving and proliferating in a serum-free medium; and/or (II) wherein the selectable marker gene is a cycloheximide resistance gene.

3. The method according to claim 1, wherein the CHO cell is at least one selected from CHO-K1, CHO-K1SV, DUKXB11, CHO/DG44, Pro-3 and CHO-S.

4. The method according to claim 2, wherein the cycloheximide resistance gene is a gene encoding a mutant of human ribosomal protein L36a.

5. The method according to claim 1,
(I) wherein the nucleotide sequences derived from a pair of Tol2 transposons are a nucleotide sequence comprising the nucleotide sequence shown in SEQ ID NO:2 and the nucleotide sequence shown in SEQ ID NO:3; or
(II) wherein the nucleotide sequences derived from a pair of Tol1 transposons are the nucleotide sequence shown in SEQ ID NO: 14 and the nucleotide sequence shown in SEQ ID NO:15.

6. A suspension mammalian cell capable of producing an antibody or an antibody fragment thereof;
(I) into which an expression vector comprising a gene fragment comprising a DNA encoding an antibody or an antibody fragment thereof and a selectable marker gene, and transposon sequences at both terminals of the gene fragment, is introduced, to integrate the gene fragment inserted between a pair of the transposon sequences into a chromosome; or
(II) into which an expression vector (a) comprising a gene fragment comprising a DNA encoding an antibody or an antibody fragment thereof and a selectable marker gene, and transposon sequences at both terminals of the gene fragment, and an expression vector (b) comprising a DNA encoding a transposase which recognizes the transposon sequences and has activity of transferring the gene fragment inserted between a pair of the transposon sequences into a chromosome, is introduced, to integrate the gene fragment inserted between a pair of the transposon sequences into the chromosome,
wherein a pair of the transposon sequences are nucleotide sequences derived from a pair of Tol1 transposons or nucleotide sequences derived from a pair of Tol2 transposons, and wherein the suspension mammalian cell is at least one selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension-culture.

7. The cell according to claim 6,
(I) wherein the cell is a cell capable of surviving and proliferating in a serum-free medium; and/or (II) wherein the selectable marker gene is a cycloheximide resistance gene.

8. The cell according to claim 7, wherein the CHO cell is at least one selected from CHO-K1, CHO-K1SV, DUKXB11, CHO/DG44, Pro-3 and CHO-S.

9. The cell according to claim 7, wherein the cycloheximide resistance gene is a gene encoding a mutant of human ribosomal protein L36a.

10. The cell according to claim 6,
(I) wherein the nucleotide sequences derived from a pair of Tol2 transposons are the nucleotide sequence shown in SEQ ID NO:2 and the nucleotide sequence shown in SEQ ID NO:3; or
(II) wherein the nucleotide sequences derived from a pair of Tol1 transposons are the nucleotide sequence shown in SEQ ID NO: 14 and the nucleotide sequence shown in SEQ ID NO:15.

11. The antibody expression according to claim 1 or 9, comprising a gene fragment comprising a DNA encoding an antibody or an antibody fragment thereof and a selectable marker gene, and a pair of transposon sequences at both terminals of the gene fragment,
(I) wherein the nucleotide sequences derived from a pair of the Tol2 transposons are the nucleotide sequence shown in SEQ ID NO: 2 and the nucleotide sequence shown in SEQ ID NO: 3; or (II) wherein the nucleotide sequences derived from a pair of the Tol1 transposons are the nucleotide sequence shown in SEQ ID NO: 14 and the nucleotide sequence shown in SEQ ID NO: 15.

12. The method according to claim 1, wherein the antibody is a monoclonal antibody.

13. The method according to claim 12, wherein the monoclonal antibody is a monoclonal antibody selected from a chimeric antibody, a humanized antibody and a human antibody.

14. The cell according to claim 6, wherein the antibody is a monoclonal antibody.

15. The cell according to claim 14, wherein the monoclonal antibody is a monoclonal antibody selected from a chimeric antibody, a humanized antibody and a human antibody.

16. The expression vector according to claim 11, wherein the antibody is a monoclonal antibody.

17. The expression vector according to claim 13, wherein the monoclonal antibody is a monoclonal antibody selected from a chimeric antibody, a humanized antibody and a human antibody.

18. The expression vector according to claim 11 or 16, wherein the expression vector is used for producing the antibody or the antibody fragment thereof.

* * * * *